US007795039B2

(12) United States Patent  
Spira et al.

(10) Patent No.: US 7,795,039 B2
(45) Date of Patent: Sep. 14, 2010

(54) ELECTRONIC DEVICE FOR COMMUNICATION WITH LIVING CELLS

(75) Inventors: Micha Spira, Jerusalem (IL); Shlomo Yitzchaik, Jerusalem (IL); Joseph Shappir, Mevasseret Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 945 days.

(21) Appl. No.: 10/560,315

(22) PCT Filed: Jun. 10, 2004

(86) PCT No.: PCT/IL2004/000502

§ 371 (c)(1),
(2), (4) Date: Sep. 12, 2006

(87) PCT Pub. No.: WO2004/109282

PCT Pub. Date: Dec. 16, 2004

(65) Prior Publication Data

US 2007/0099173 A1    May 3, 2007

Related U.S. Application Data

(60) Provisional application No. 60/477,037, filed on Jun. 10, 2003.

(51) Int. Cl.
*G01N 33/543* (2006.01)
(52) U.S. Cl. .................................................. 436/518
(58) Field of Classification Search ........................ None
See application file for complete search history.

(56) References Cited

U.S. PATENT DOCUMENTS

| 4,546,083 | A | * | 10/1985 | Meyers et al. ................ 435/400 |
| 5,795,860 | A | * | 8/1998 | Witt et al. ........................ 506/9 |
| 6,465,331 | B1 | * | 10/2002 | Keeth et al. ................... 438/479 |
| 6,846,654 | B1 | * | 1/2005 | Blackburn et al. ............ 435/7.1 |
| 7,270,973 | B2 | * | 9/2007 | Singh et al. ..................... 435/18 |
| 2002/0053915 | A1 | | 5/2002 | Weaver et al. |

FOREIGN PATENT DOCUMENTS

| DE | 198 41 337 C1 | | 9/1999 |
| EP | 2000097899 | | 4/2000 |
| EP | 2001156398 | | 6/2001 |
| WO | WO 00/51191 | * | 8/2000 |
| WO | WO 01/25769 A2 | | 4/2001 |
| WO | WO 03/104789 | * | 12/2003 |
| WO | WO 03/104789 A1 | | 12/2003 |
| WO | WO 2004/044573 A1 | | 5/2004 |
| WO | 2004109282 A1 | | 12/2004 |

OTHER PUBLICATIONS

Stett, A., Muller, B., Fromherz, P., "Two-way silicon- neuron interface by electrical induction", *Phys. Rev. B.*, 55: 1779-1781 (1997).
Fromherz, P., "Electrical Interfacing of Nerve Cells and Semiconductor Chips", *Chemphyschem.* 3:276-84; 2002.
Weis R., and P. Fromherz. "Frequency dependent signal-transfer in neuron-transistors", Physical Review E. 55:877-889; Jan. 1997.
Weis R., B. Muller, and P. Fromherz, "Neuron Adhesion on a Silicon Chip Probed by an Array of Field-Effect Transistors", Physical Review Letters. 76:327-330; Jan. 8, 1996.
Kandel, E.R. 2001, "The Molecular Biology of Memory Storage: A Dialog Between Genes and Synapses", Bioscience Report vol. 21, No. 5 pp. 565-611; Oct. 2001.
Kandel, E.R. 2001, "The Molecular Biology of Memory Storage: A Dialogue Between Genes and Synapses", Science. 294:1030-8; Nov. 2, 2001.
Zeck G., and P. Fromherz., "Noninvasive neuroelectronic interfacing with synaptically connected snail neurons immobilized on a semiconductor chip", Proc Natl Acad Sci U S A. 98:10457-62, Aug. 28, 2001.
Aderem, A., and D.M. Underhill. 1999, "Mechanisms of phagocytosis in macrophages", Annu Rev Immunol. 17:593-623.
May, R.C., and L.M. Machesky, 2001, "Phagocytosis and the actin cytoskeleton", J Cell Sci. 114:1061-77.
Indik Z. et al., 1991, "Human Fc, RII, in the absence of other Fc, receptors, mediates a phagocytic signal", J Clin Invest. 88:1766-71.
Blystone S.D. et al., Nov. 1994, "Integrin alpha v beta 3 Differentially Regulates Adhesive and Phagocytic Functions of the Fibronectin Receptor alpha 5 beta 1", J Cell Biol. 127:1129-37.
Stahl P.D., and R.A. Ezekowitz, 1998, "The mannose receptor is a pattern recognition receptor involved in host defense", Current Opinion in Immunology 10:50-5.
Dahlgren K et al., Immobilization of Enzymes Based on Hydrophobic Interaction. I. Preparation and Properties of a β-Amylase Adsorbate; Biotechnology and Bioengineering, vol. XVIII, pp. 1573-1588 (1976).
Critchley D.R., 2000, "Focal adhesions—the cytoskeletal connection", Current Opinion in Cell Biol. 12:133-9.
Heiple J.M. et al., 1990, "Macrophages Form Circular Zones of Very Close Apposition to IgG-Coated Surfaces", Cell Motility Cytoskeleton. 15:260-70.
Willner, I.; Katz, E. Angew. "Enzyme electrodes allow the production of more types of products" Chem., Int. Ed. 2000, 39, 1180-1218.
Yang, M. et al., Anal. "Acoustic Network Analysis as a Novel Technique for studying protein adsorption and Denaturation at Surfaces" Chem. 1993, 65, 3713-3716.
Caruso F. et al., J. "Characterization of Ferritin Adsorption onto Gold" Colloid Interface Science 1997, 186, 129-140.

(Continued)

*Primary Examiner*—Ann Y Lam
(74) *Attorney, Agent, or Firm*—Browdy and Neimark, PLLC

(57) ABSTRACT

The present invention provides a surface-substrate for adherence of cells thereto. The surface-substrate comprises at least one micronail structure protruding from the surface, at least a region of the micronail having cellular-internalization promoting properties. The invention also provides an electronic device comprising a transistor structure, in which a gate electrode is formed with the at least one micronail protruding from the surface thereof.

43 Claims, 13 Drawing Sheets

OTHER PUBLICATIONS

Razumas V., Arnebrant T., J. "Direct electrochemistry of microperoxide—11 at gold electrodes modified by self-assembled monolayers of 4,4'-ditihiodipyridine and 1-octadecanethiol" Electroanalytical Chemistry. 1997, 427, 1-5.

Moulin A. M. et al., "Measuring Surface-Iinduces Conformational Changes in Protein" Langmuir 1999, 15, 8776-8779.

Armstrong F. A. et al., "Reaction of electron-transfer proteins at electrodes" Q. ReV. Biophys. 1986, 18, 261-322.

Ulman A., "Formation and Structure of Self-Assembled Monolayers" Chem. Rev. 1996, 96, 1533-1554.

Prime K. L., Whitesides G. M., J. Am. "Adsorption of Protein onto Surfaces Containing End-Attached Oligo (ethylene oxide): A Model System Using Self-Assembled Monolayers" Chem. Soc. 1993, 115, 10714-10721.

Lahiri J. et al., "A Strategy for the Generation of Surfaces Presenting Lligands for Studies of Binding based on an Active Ester as a Common Reactive Intermediate: A Surface Plasmon Resonance Study" Anal. Chem. 1999, 71, 777-790.

Spinke J. et al., "Molecular Recognition at Self-Assembled Monolayers: Optimization of surface functionalization" J. Chem Phys. Nov. 1, 1993, 99, 7012-7019.

Spinke J. et al., "Molecular Recognition at Self-Assembled Monolayers: The Construction of Multicomponent Multilayers" Langmuir 1993, 9, 1821-1825.

Jain A., Huang S. G., Whitesides, "Lack of Effect of the Length of Oligoglycine and Oligo (ethylene glycol)-Drives para-Substituents on the Affinity of Benzenesulfonamides for Carbonic Anhydrase II in Solution" G. M. J. Am. Chem. Soc. 1994, 116, 5057-5062.

Mrksich M., Grunwell J. R., Whitesides "Biospecific Adsorption of carbonic Anhydrase to Self-Assembled Monolayers of Alkanethiolates That Present Benzenesulfonamide Group on Gold" G. M., J. Am. Chem. Soc. 1995, 117, 12009-12010.

Frey B. L. et al., "Control of the specific adsorption of Protein onto Gold Surfaces with poly($^L$-Iysine) Monolayers" Anal. Chem. 1995, 67, 4452-4457.

Schlereth D. D., "Preparation of gold surface with biospecific affinity for NAD(H)-dependent lactate dehydrogenase" Sens. Actuators, B 1997, 43, 78-86.

Schlereth D. D., Kooyman R. P. H., Self-assembled monolayers with biospecific affinity for NAD(H)-dependent dehydrogenases: characterization by surface plasmon resonance combined with electrochemistry 'in situ' J. Electroanal. Chem. 1998, 444, 231-240.

Perez-Luna V. H. et al, "Molecular Recognition between Genetically Engineered Streptavidin and Surface-Bound Biotin" J. Am. Chem. Soc. 1999, 121, 6469-6478.

Porath J. et al., "Metal Chelate affinity chromatography, a new approach to protein fractionation" Nature 1975, 258, 598-599.

Mosbach G. R. et al., "Protein of Cellulose-Bound Enzymes" Methods Enzymol. 1976, 44, 53-65.

Mattiasson B., "Affinity Immobilization" Methods Enzymol. 1988, 137, 647-656.

Bastida A. et al, "A Single Step Purification, Immobilization, and Hyperactivation of Lipases via Interfacial Adsorption on Strongly Hydrophobic Support" Biotechnol. Bioeng. 1998, 58, 486-493.

Turkova J, "Oriented immobilization of biologically active protein as a tool for revealing protein interactions an function" J. Chromatogr., B 1999, 722, 11-31.

Willner I. et al, "Electrical Wiring of Glucose Oxidase by Reconstitution of FAD-Modified Monolayers Assembled onto Au-Electrodes" J. Am. Chem. Soc. 1996, 118, 10321-10322.

Schmidt H.-L., Schuhmann W., "Reagentless oxidoreductase sensors" Biosens. Bioelectron. 1996, 11, 127-135.

Katz E. et al., "Reconstitution of the quinoprotein glucose dehydrogenase from its apoenzymeon a gold electrode surface modified with monolayer of pyrroloquinoline quinine" J. Electroanal. Chem. 1994, 368, 165-171.

Guo L.-H. et al, "Photo-active and electro-active protein films prepared by recostitution with metalloporphyrins self-assembled on gold" J. Mater. Chem. 1996, 6, 369-374.

Katz E. et al., "Electrical contact of redox enzymes with electrodes: novel approaches for amperometric biosensors" Bioelectrochem. Bioenerg. 1997, 42, 95-104.

Willner I. et al, "Assembly of functionalized monolayers of redox protein on electrode surfaces: novel bioelectronic and optobioelectronic system" Biosens. Bioelectron. 1997, 12, 337-356.

Gorton L. et al, "Direct electron transfer between heme-containing enzymes and electrodes as basis for third generation biosensors" Anal. Chim. Acta 1999, 400, 91-108.

Hodneland, C. D.; Lee, Y.-S.; Min, D.-H.; Mrksich, M. Proc."Selective immobilization of protein to self-assembled monolayers presenting active site-directed capture ligands" Natl. Acad. Sci. U.S.A. 2002, 99, 5048-5052.

Gilardi, G.; Fantuzzi, A.; Sadeghi, S. J. "Engineering and design in bioelectrochemestry of metalloproteins" Curr. Opin. Stuct. Biol. 2001, 11, 491-499.

Pierrat, O.; Lechat, N.; Bourdillon, C.; Laval, J. M. "Electrochemical and Surface Plasmon Resonance Characterization of the Step-by-Step Self-Assembly of a Biomimetric Structure onto an Electrode Surface" Langmuir 1997, 13, 4112-4118.

Darder, M.; Casero, E.; Pariente, F.; Lorenzo, E. "Biosensors Based on Membrance-Bound Enzymes Immobilized in a 5-(Octyldithio)-2-nitirobenzoic Acid Layer on Gold Electrodes" Anal. Chem. 2000, 72, 3784-3792.

W. C. Wildering, P. M. Hermann, A. G. M. Bulloch "Neurite Outgrowth, RGD-Dependent, and RCG-Independent Adhesion of Identified Molluscan Motoneurons on Selected Substrates" J Neurobiol 35: 37-52, 1998.

Sfez R. et al., "Polyaniline Monolayer Self-Assembled on Hydroxyl-Terminated Surfaces" Langmuir 2001, 17(9), 2556-2559.

Turyan, I.; Mandler, D., "Two-Dimensional Polyaniline Thin Film Electrodeposited on a Self-Assembled Monolayer" J. Am. Chem. Soc. 1998, 120, 10773-10742.

Ma X L et al: "Microstructural characterization of Si cones fabricated by Ar<+>-sputtering Si/Mo targets" Journal of crystal Growth, North Holland Publishing, Amsterdam, NL vol. 234, No. 4, Feb. 2002, pp. 654-659.

Fromherz P: "Semiconductor chips with ion channels, nerve cells and brain", Physica e Elsevier Netherlands, vol. 16 No. 1, Jan. 2003, pp. 24-34.

* cited by examiner

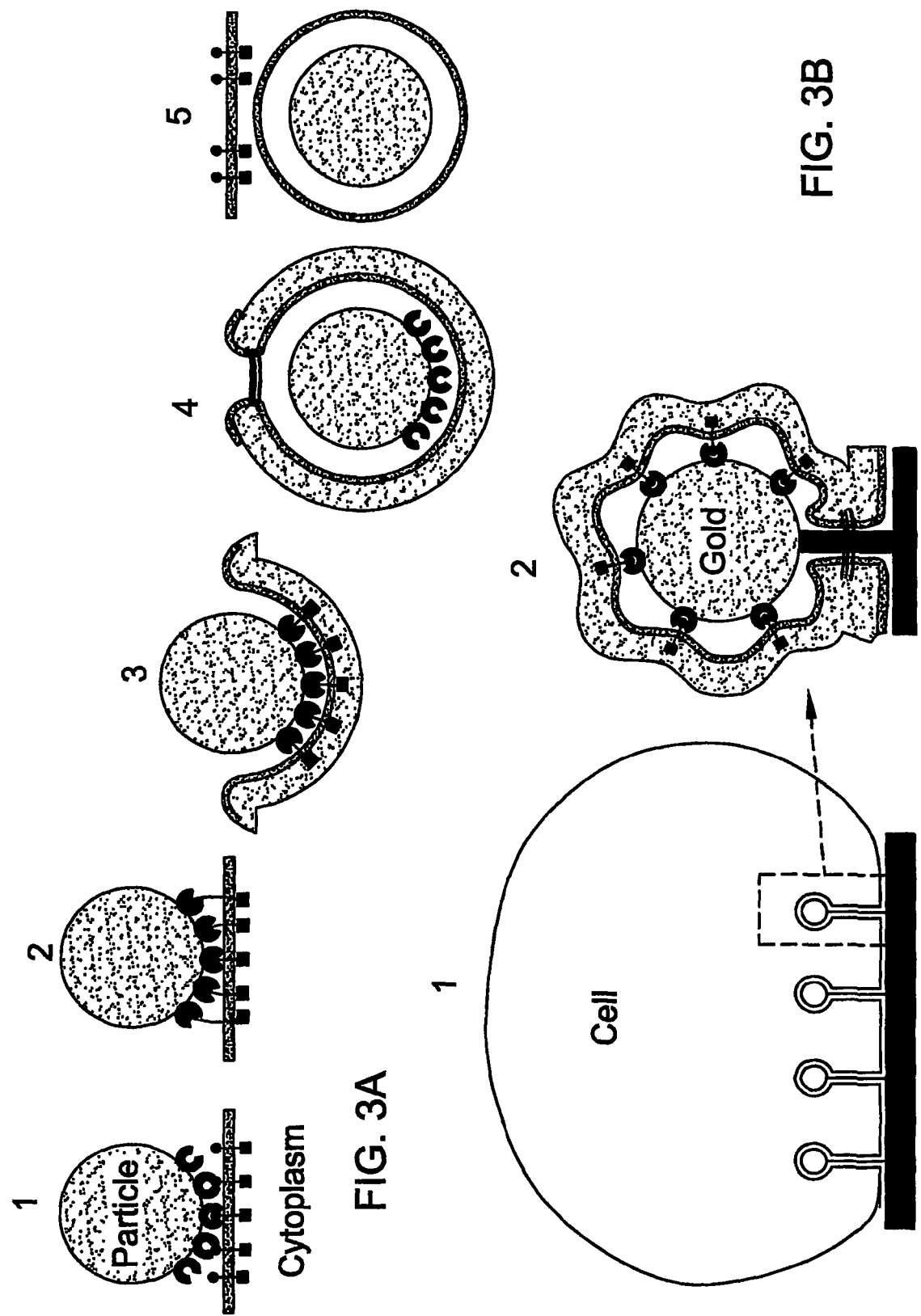

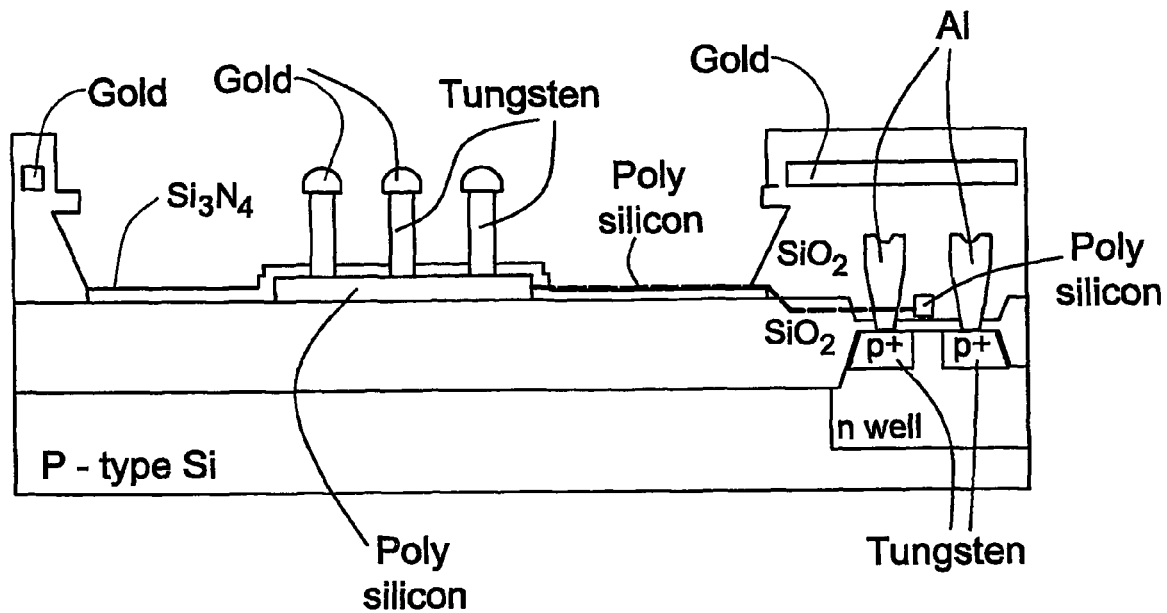
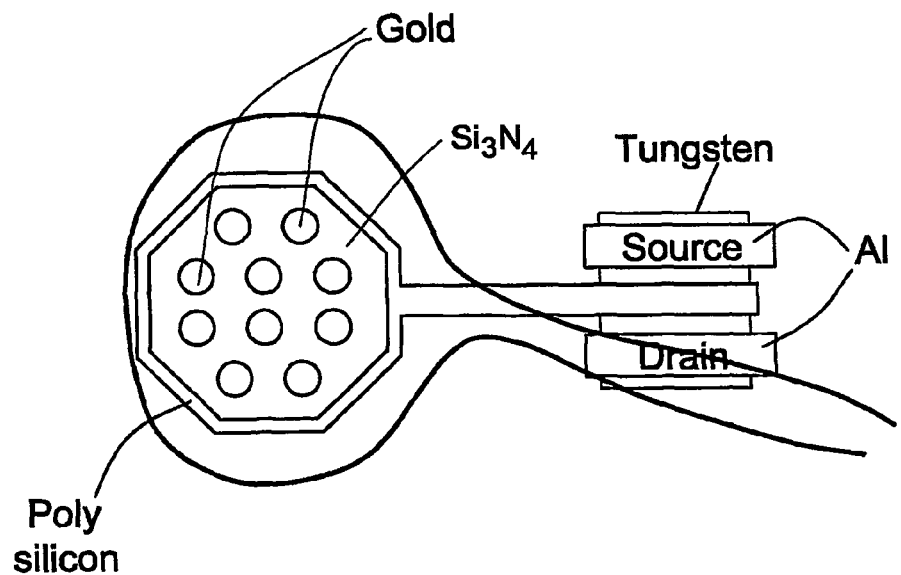
FIG. 5

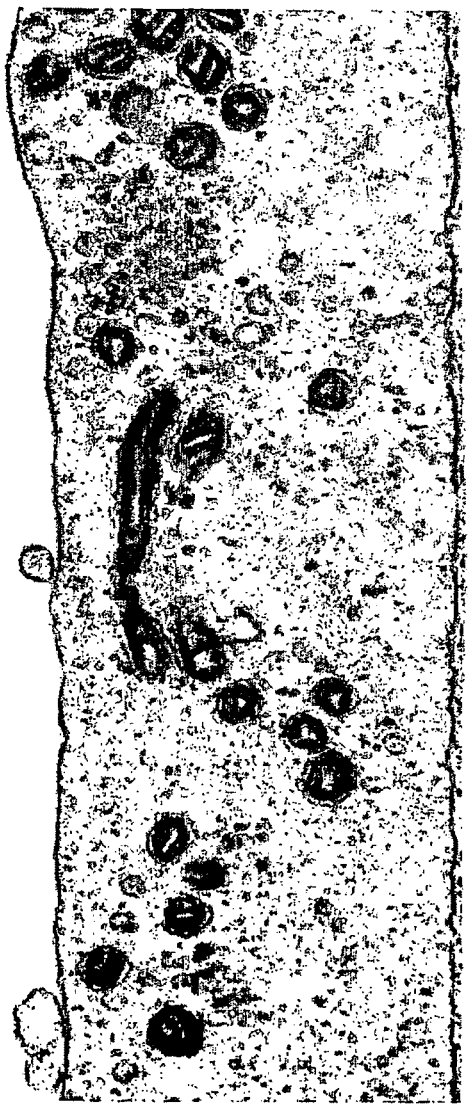
FIG. 13

ELECTRONIC DEVICE FOR COMMUNICATION WITH LIVING CELLS

FIELD OF THE INVENTION

This invention is generally in the field of bio-molecular electronics, and relates to an electronic device for communication with living cells.

REFERENCES

The following publications are believed to be relevant to the Background section of the specification:
1. Stett, A., Muller, B., Fromherz, P., "Two-way Neuron-Silicon Interface by Electrical Induction", *Phys. Rev. B.*, 55:1779-1781 (1997);
2. Fromherz, P., "*Electrical interfacing of nerve cells and semiconductor chips*", Chemphyschem. 3:276-84 (2002);
3. Weis. R. and P. Fromherz, "*Frequency dependent signal-transfer in neuron-transistors*", Physical Review E. 55:877-889 (1997);
4. Weis. R., B. Muller, and P. Fromherz, "*Neuron adhesion on a silicon chip probed by an array of field-effect transistors*", Physical Review Letters. 76:327-330 (1996);
5. Zeck G., and P. Fromherz, "*Noninvasive neuroelectronic interfacing with synaptically connected snail neurons immobilized on a semiconductor chip*", Proc Nat.1Aca.d Sci USA. 98:10457-62 (2001);
6. Indik Z. et al., 1991, "Human Fc gamma RII, in the absence of other Fc gamma receptors, mediates a phagocytic signal", *J. Clin. Invest.* 88:1766-71 (1991);
7. Stahl P. D., and R. A. Ezekowitz, "The mannose receptor is a pattern recognition receptor involved in host defense", *Curr. Opin. Immunol.* 10:50-5 (1998);
8. Willner, I.; Katz, E. *Angew. Chem., Int. Ed.,* 39:1180-1218 (2000);
9. Yang, M. et al. *Anal. Chem.* 65:3713-3716 (1993);
10. Ulman A., *Chem. Rev.,* 96:1533-1554 (1996);
11. Prime K. L., Whitesides G. M., *J. Am. Chem. Soc.,* 115:10714-10721 (1993);
12. Spinke J. et al., *J. Chem Phys.,* 99:7012-7019 (1993);
13. Porath J. et al., *Nature,* 258:598 (1975);
14. Willner I. Et al, *J. Am. Chem. Soc.* 1996, 118:10321-10322;
15. W. C. Wildering, P. M. Hermann, A. G. M. Bulloch, *J. Neurobiol.* 35: 37-52, (1998);
16. WO 00/51191;
17. Turyan, I., Mandler, D., *J. Am. Chem. Soc.,* 120:10773 (1998).

BACKGROUND OF THE INVENTION

Interaction between neurons and electronic devices has been in existence for several decades for a plurality of purposes. During the past decades, these interactions were usually achieved by inserting an electrode assembly (single electrode or an array of electrodes) into the neurons, or placing an electrode assembly in the vicinity of the neurons' membranes, so as to detect voltage changes. The detection electrode assembly can also be used for the stimulation of neurons.

Attempts have been made to provide coupling between a neuron and a transistor device [1], utilizing a bidirectional interface between the ionic conduction of the neuron and the electronic conduction of the transistor, achieved by two separate modalities.

WO 00/51191 [17] (having the same inventors as in the present application) discloses an electrical junction between a transistor and a neuron, transistors to be used in said junction, and an artificial chemical synapse. "Chemical synapse" is a junction between a cell, which secretes an agent, and a transistor bearing receptors for the agent, wherein binding of the agent to the receptor changes an electrical property of the transistor.

SUMMARY OF THE INVENTION

The present invention is based on the finding that a tight physical linkage can be formed between cells and surface-substrates by taking advantage of the cell's natural property to internalize elements of the extracellular word by phagocytosis/pinocytosis or endocytosis. This basic property is utilized to provide a tight physical linkage between the cells and the surface by constructing the surface to have nano-to micro scale protrusions in the form of "micronail". Beyond their size the micronail have cellular-internalization promoting properties. These properties are either due to inherent properties of the material denoted by the material from which the protruding micronail is formed or is coated by (such as metal), or due to immobilizing onto the micronail of moieties which promote cellular internalization. By this finding, the protrusions of the surface are internalized into the cell and the cellular membrane is wrapped around it, as will be explained in more detail hereinbelow, and by this the cell is adhered with a strong physical tight contact onto the surface. In addition to that the head of the micronail may be decorated with material that can lead to the penetration of the nail into the cytoplasm. For example, penetration of the nail can be used also as a micro syringe to deliver materials either to the plasma membrane or intracellularely.

This tight physical contact may be used for many purposes. By one embodiment, where it is important to minimize the movement or change of spatial position of a cell on a surface, for example, for various manipulations of the cells (for research purposes, for photography purposes, etc.), the adherence may be into "inert" surface merely for the purpose of limiting the spatial change, or movement of cells.

In accordance with a preferred embodiment of the invention, the physical tight coupling is utilized to provide a good electrical and/or chemical coupling and adherence of cells into a surface which is a part of an electrode. The electrode is part of an electrodes arrangement of an electronic device, which may be utilized either for bidirectional electrical communication with a cell (sensing or stimulating cells) or alternatively with electrical devices which can sense the presence of various chemical components which are secreted from cells, or defuse into the solution from other sources, as will be explained herein below.

Thus, the present invention provides a surface-substrate for adherence of cells thereto comprising:

at least one micronail structure protruding from the surface, at least a region of said micronail having cellular-internalization promoting properties.

The term "surface-substrate" refers to a surface, which may be a stand-alone construct used to minimize movement of cells, or a part of a more elaborate construction (such as an electrode, or an electric device) which has either unique inherent chemical properties due to the material from which it is made and its construction in the form of protrusions, or which has been chemically modified (for example by binding of molecules) to promote adherence of cells thereto.

The term "micronail" in the context of the present invention refers to a micrometer or nanometer scale protrusion from the surface of the surface-substrate. The surface comprises at least one micronail structure, but it typically comprises a plurality of micronail structures which may all be identical to each other in their chemical properties or which may differ from each other. The micronails which may be distributed at a distance from each other so that each electrode serves as a base for a single or many micronails is present on a single or many electronic component construct (for example each micronail structure is present on a single gate electrode) or may be distributed as specially constructed clusters, which can be internalized by a single cell.

The term "cellular-internalization promoting properties" refers to chemical or chemical/structural properties of the micronail which induce its partial or total internalization by phagocytosis, pinocytosis or endocytosis, into cells.

The cellular-internalization promoting properties may be the inherent property of the micronail material (for example, where the micronail is made of, or coated with a metal, for example, a metal selected from gold, copper, aluminum, platinum, silver, alloys of these metals or combinations thereof).

Alternatively, the properties for promoting a cellular internalization of the micronail are denoted in the micronail by immobilizing thereto biological moieties which promote such internalization.

The micronail may have a uniform structure. According to a preferred embodiment of the invention, the micronail is composed of two chemically distinct regions: a head portion, and a base portion. Typically, the cellular-internalization promoting properties are a property of the head portion, although during the process of internalization many times both the head and the base portion are internalized by the cell.

The term "internalization" refers to the fact that at least a part of the micronail traverses the plasma membrane of the cell and is "engulfed" by the membrane (while the micronail is still attached to the surface).

The term "promoting" means increase of the chance of internalization of a micronail with said properties (metal/biological molecules attached) as compared to micronails without these properties (non-metal/lacking molecules). It does not mean that all micronails having these properties are internalized as this biological activity has a certain statistical chance of occurring or not occurring regardless of these properties.

The term "cellular-internalization-promoting biological moieties" refers to any biological molecule, complex of biological molecules, or fragments of biological molecules, which increase the probability of a component, coated therewith or attached thereto, to be internalized by the cell. Generally, these biological moieties are divided into the following groups:

1. hydrolytic enzymes that facilitate degradation of extracellular matrix, thus "cleaning" the debris coating the cell to be adhered and increasing the probability of internalization;
2. molecules that recognize plasma membranes components located on the external surface of the plasma membrane of cells, which enable an intimate, and tight recognition interaction between the molecules and the plasma membrane of the cell, and thus promote internalization;

or a combination of both.

It should be explained, that the internalization is a relatively "spontaneous" event, and the cellular-internalization induction is achieved by elimination of obstacles of the extracellular matrix which come between the cellular membrane and the micronail (by the use of hydrolytic enzymes) or by promoting the formation of a tight interaction by the plasma membrane and nail head, or by activation of specific receptors that recruit the phagocytotic machinery.

Hydrolytic enzymes may be any enzymes which degrade at least one extracellular component such as polysaccharides degrading enzymes, proteinases, and lipid degrading enzymes.

Preferably, as these hydrolytic enzymes may damage in the long run cells attached to the surface-substrate of the invention, these enzymes are connected to the micronail through a spacer which is biodegradable, so that the time span of their activity is short, and after a while they are spontaneously detached from the surface-substrate.

The term "molecules that recognize plasma membrane components" refers to any member of pair forming group, the other member of which is a plasma membrane component, the membrane component may be a protein, a lipid, a polysaccharide, a glycoprotein, etc. Examples of such molecules are ligand of plasma membrane receptors (or receptor binding parts of said ligand), receptors that recognize plasma membrane components; lectins that bind to plasma membrane glycoproteins; antibodies that recognize plasma membrane components (either proteins or non-proteins) or binding fragments of said antibodies; integrins that recognize short linear amino acids present in extracellular proteins, or a combination of two or more of these proteins.

In order to enhance the adherence of the cell to the surface-substrate of the invention, it is preferable that in addition to the properties that induce cellular internalization, the surface also contains an additional "adhesion molecule" which tightens the connection between the cell and the surface.

The adhesion molecules preferably should be present either in the base portion of the micronail, or on the region of the surface surrounding the base portion of the protruding micronail.

The adhesion molecules may be in the form of a charge monolayer, such as a monolayer of polylysine, which is known to promote adhesion of neurons to a substrate.

The description above is suitable for any surface-substrate in accordance with the invention which purpose is to form a tight physical connection between the cells and the surface.

However, the surface may also be adapted to be part of a cell-communicating component of an electrode.

The term "cell communicating component" refers to the part of the electrode that is in physical contact and in electrical communication (for sensing and/or stimulating purposes) with a cell.

Preferably, the electrode is an electrode which is intended to communicate with cells having electric properties, or having physiological responses to electricity, such as neurons, muscle cells, and cells of secreting glands. The electrode may be a regular electrode or a gate electrode. Where the surface-substrate in accordance with the claims is adapted to form the cell communicating component of the electrode the base portion of each micronail should be electrically isolated from its surrounding so as to decrease "shunting" to the electrolyte containing solution in which the cell is present. For example, in a gate electrode of a MOS transistor, the micronail may be a polysilicon rod (being an integral part of the polysilicon gate electrode) which is isolated from its surrounding by an internal oxide layer.

The present invention also concerns an electrode comprising the surface-substrate adapted to form the cell communicating component of an electrode, as well as a gate electrode comprising the surface-substrate adapted to form the cell communicating component of a gate electrode.

Both the regular electrode and the gate electrode described as above, may form a part of an electric device for electrical communication with a cell, preferably a cell which is either electrically active or a cell having physiological response to electricity, such as muscle cells, neurons and cells of secreting glands.

The term "electrical communication" refers to any relationship between an electrode or cells selected from the following:
1. detection of the presence of current in cells by the electrodes or detection of current changes;
2. detection the changes in potential on plasma membranes of cells or changes in said potential;
3. providing current to cells;
4. applying an electric field to cells.
5 a combination of two or more of the above.

Electrical communication using such a device may be carried out for a variety of purposes, such as for basic research purposes; for the construction of biomedical devices; especially those which need a functional link between nerves or muscles to electric components of robotic prosthesis, in order to provide amputees with robotic prosthesis that is controlled by neurons or muscles; in order to restore vision after retinal or optic nerve damage, in order to electrically stimulate cells of secreting glands to secrete required components, etc.

By another alternative, the surface-substrate of the invention is used to form a part of an electrode which can sense the presence of an analyte in a sample. For example, the surface-substrate of an invention may be a part of an electrode which is further coated with a layer of immobilized recognition molecules, that in the presence of a cell secreted component, catalyze a reaction that causes releases of ion in a media surrounding said recognition molecule. The secretion of said ions causes an electrical change in the electrode which can be monitored as an indication of the presence of the cell secreted component.

The term "recognition molecule" refers to any molecule that can both recognize a cell secreted component, and simultaneously catalyze a reaction that causes a release of ions. Typically, such recognition molecules are enzymes or peptides.

The term "cell secreted component" refers to any component which is secreted by cells, a specific example being neurotransmitters such as acetylcholine glutamate, GABA and serotonin. For example, where the cell secreted component is acetylcholine, the recognition molecule is acetylcholine esterase which can release ions sensed by the electrode.

The recognition molecules are typically immobilized onto the electrode via linker molecules such as conjugated or unconjugated, aliphatic, aromatic or heteroaromatic molecules having at least one functional group which can be covalently bound either to the surface of the surface-substrate or to the recognition moieties or to both.

In one embodiment, the distance between the recognition molecules and the surface of the coated gate is smaller than 15 Å.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 3A and 3B schematically illustrate the main principles of the phagocytosis phenomenon, by showing schematic presentations of the cellular mechanisms that underlie phagocytosis (FIG. 3A), and its comparison to the engulfment of a micronail (FIG. 3B);

FIG. 4B corresponds to the induction of an endocytotic profile by a particle; FIG. 4C corresponds to the endocytotic profile; and FIG. 4D corresponds to a coated vesicle containing a cell fragment;

FIGS. 5 and 6 illustrate an electronic device (transistor) according to the invention utilizing a gate electrode formed with micronails which are protruding from gate electrode surface, wherein FIG. 5 shows an over view of the micronails configuration on the floating gate, and FIG. 6 shows the scaled cross-section of the 'nail' structures.

FIG. 13 presents electron microscopy image showing the interface between Aplysia's plasma membrane and a monolayer of 5 nm Au particles self-assembled with 2D-PAN monolayer on a glass substrate.

GENERAL DESCRIPTION OF THE INVENTION

Figure 1:
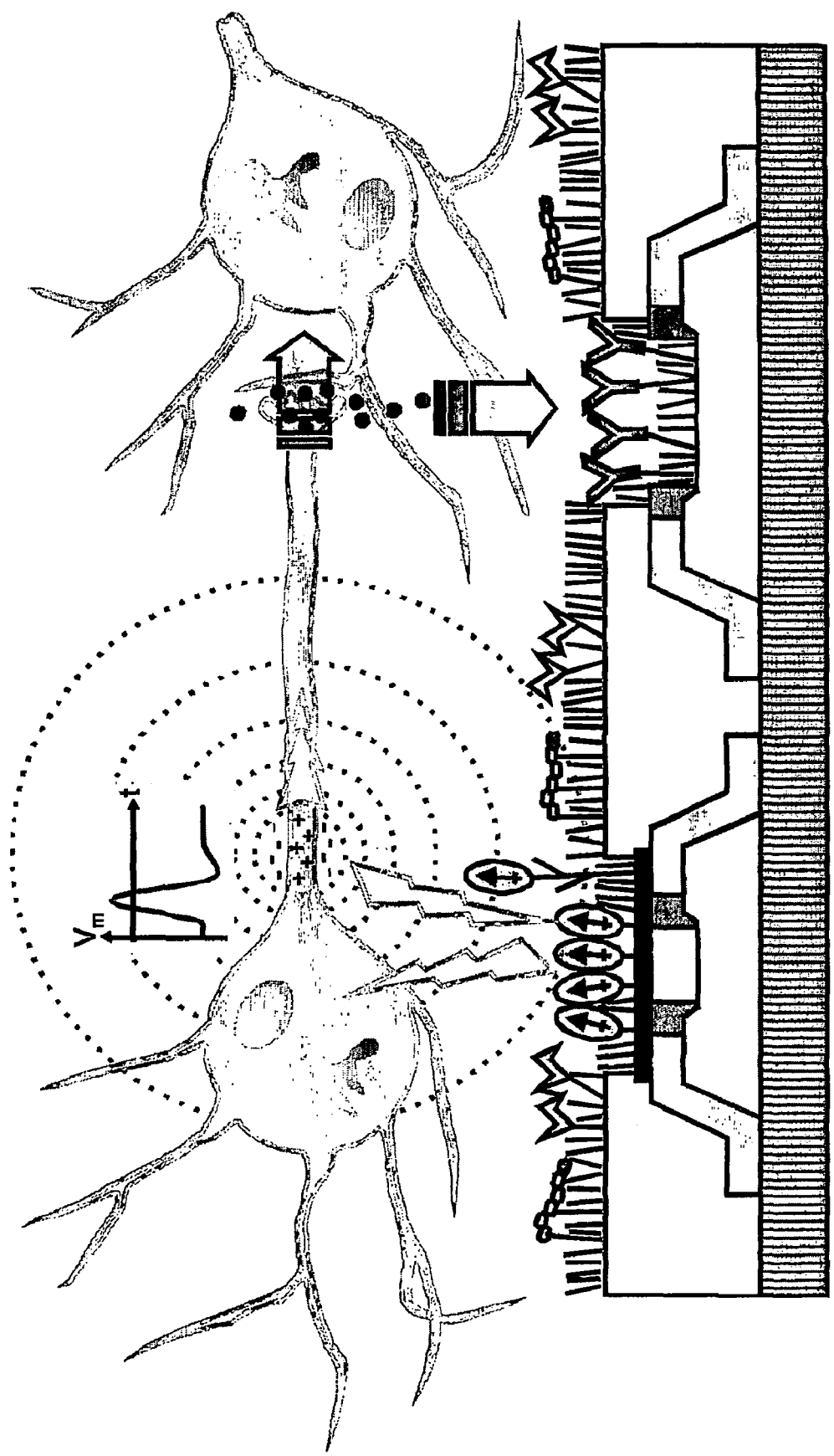
FIG. 1 is a schematic illustration of a neuroelectronic hybrid system.

By one aspect the present invention merely provides a tight physical connection to an "inert" surface-substrate.

By another aspect the present invention provides reliable and durable bi-directional electrical as well as chemical communication (functional linking) between cells (such as neurons) and substrate-surfaces which are part of electronic devices. This generic technology can serve as the base for the construction of biomedical devices that can, for example, be used to functionally link nerves to robotic prosthesis and thus provide amputees with robotic prosthesis that are controlled by the brain, functionally link damaged neuronal networks, restore vision after retinal or optic nerve damage, stimulation of secretor, etc. It can also be used to screen drugs or for the development of ex-vivo hybrids between electronic devices, cells and molecules.

The invention is based on analysis of parameters and mechanisms that control the degree of coupling between biological cells such as neurons and surfaces (such as those constituting) electronic devices, and identification of critical previously unforeseen basic scientific and technological problems that had to be solved in order to advance and filly implement the technology of neuro-electronic hybrid devices, and provide technical solutions for these problems.

The invention harnessed the basic properties of cells to identify, preferentially adhere and then to internalize elements of the extracellular world by phagocytosis (the term phagocytosis may interchangeably be used with the terms pinocytosis or endocytosis). It was found that by making the electronic device (e.g. gate electrode of a transistor) with protrusions having special properties, the phagocytosis leads to the internalization of these protrusions, thereby providing optimal coupling between the surface and the cell. The basic properties of biological cells, together with a novel design of the surface (such as electrode), as well as by use of tailored surface chemistry, provide for reducing the cell's mobility and producing tight physical linkage between cells and the surfaces, for example, of electronic or chemical devices and thereby producing tight electrical and/or chemical coupling.

As mentioned above, the electrode surface morphology is designed in a novel, rough form, consisting of protrusions projecting from the electrode surface. These protrusions are also termed hereinafter "micronails" or "nails" by one option, and they comprise a rod- or stem-like "base" portion and may also comprise a "head" portion, and the nails length is preferably ranging between tens of nanometers to thousands of nanometers. The diameters of the nails at the base portion range between tens to hundreds of nanometers. The structure, dimensions and density of the micronails can be optimized to maximize the electrical and chemical coupling between the hybrid components, namely the transistor and the living cell.

The internalization of the micronails provide three major advantages: anchoring of the cell to the transistor thus reducing cell's motility; improved electrical coupling of neurons to the transistors by increasing the coupling capacitance and the increase of the resistance between the body of the biological solution and the coupling area; and improved chemical sensing (i.e., the formation of artificial "chemical synapses"). Such a novel design and fabrication of the surface morphology of a gate electrode (the protrusion of micronails) is complimented by molecularly modified surfaces that decorate differentially the different parts of the nails.

As for the chemically modified surfaces, they induce such main cellular events as: assembly of adherence junctions and internalization of the micronails' heads by membrane invagination. This can be achieved by the following ways:

The nail's head or edge carries enzymes that facilitate degradation of the extracellular matrix of the cell and thus allow the formation of intimate physical contact between the surface of the micronail's head and receptor molecules located on the external surface of the plasma membrane. These enzymes are designed to be of short lifetime.

The nail's head additionally or alternatively carries molecules that recognize plasma membrane receptors, bind to these receptors and facilitate phagocytosis or endocytosis of the micronails' head by partial internalization of the micronails by the cells.

The nail's base carries adhesion molecules that stabilize the binding of the cell's plasma membrane to the micronail's base and its surroundings.

The present invention provides a sensing element for secreted components such as neurotransmitters, based on the formation of chemical synapse composed of a neuronal presynaptic element and an electronic device that serves as a post-synaptic element. The formation of such synapses enables to link neurons to the electronic device not only by electrical signals but also by released neurotransmitters, i.e. the released neurotransmitter triggers an electronic event. Such chemical linkage opens up a novel way to link the nervous system with the electronic world and allows simulating the natural way by which neurons as well as muscles communicate with each other. It should be emphasized in this respect that the unidirectional communication between excitable cells is mainly executed by chemical synapses. To this end, the micronails containing surface of a gate electrode is coated with a variety of signaling molecules and receptor molecules that recognize and bind acetylcholine, glutamate, GABA, serotonin and others.

The inventors have developed three major components of the hybrids: electronic component, surface chemistry, and cell and neurobiology.

The electronic component is based on a transistor structure (preferably floating gate transistor as disclosed in the above-indicated publication WO 00/51191 assigned to the assignee of the present application), where the gate electrode has a special surface, which includes various types of protruding micronails. "Floating gate" is an insulated electrode of a MOS transistor on which an electric field is applied, thereby promoting an electric field to the active component of the transistor through capacitive coupling.

The surface chemistry uses advance technology to differentially link to the micronails, molecules that induce one or both two main cellular events: assembly of adherence junctions and internalization of the micronails heads by membrane invagination. These events are facilitated in the following ways: (a) The nail head is linked to hydrolytic enzymes that facilitate degradation of the extracellular matrix, thus "cleaning" the cell surface and thus allowing the formation of intimate physical contact between the micronails head's surface and receptor molecules located on the external surface of the plasma membrane; (b) The nail head may alternatively or in addition carry molecules that recognize plasma membrane components, such as membranal proteins or receptors which tether the micronail's head and facilitate phagocytosis or endocytosis of it, i.e., partial internalization of micronails by the plasma membrane; (c) The nail base on the region surrounding the base carries adhesion molecules that stabilize the binding of the cell's plasma membrane to the nails' base and/or its surroundings.

DETAILED DESCRIPTION OF THE INVENTION

1. Electronic Components

The present invention is aimed at optimizing electrical and chemical coupling between living cells, e.g. neurons and a surface-substrate which may be a part of an electronic device such as a Field Effect Transistor (FET). A FET may, for example, be a floating gate depletion type transistor as disclosed in the above-indicated publication WO 00/51191 assigned to the assignee of the present application. "Depletion type device" is an insulated-gate field-effect transistor in which free carriers are present in the channel (active component) when the gate-source voltage is zero. Channel conductivity thus exists at zero voltage between gate and source and is controlled by changing the magnitude and polarity of the gate voltage. A depletion type device is normally-on. For the normally-on depletion device, a current can flow at a zero gate potential, and the current can be increased or decreased by varying the gate voltage.

FIG. 1 illustrates a general neuroelectronic hybrid system, which provides for both electrical (left hand side) and chemical (right hand side) communication.

Figure 2:
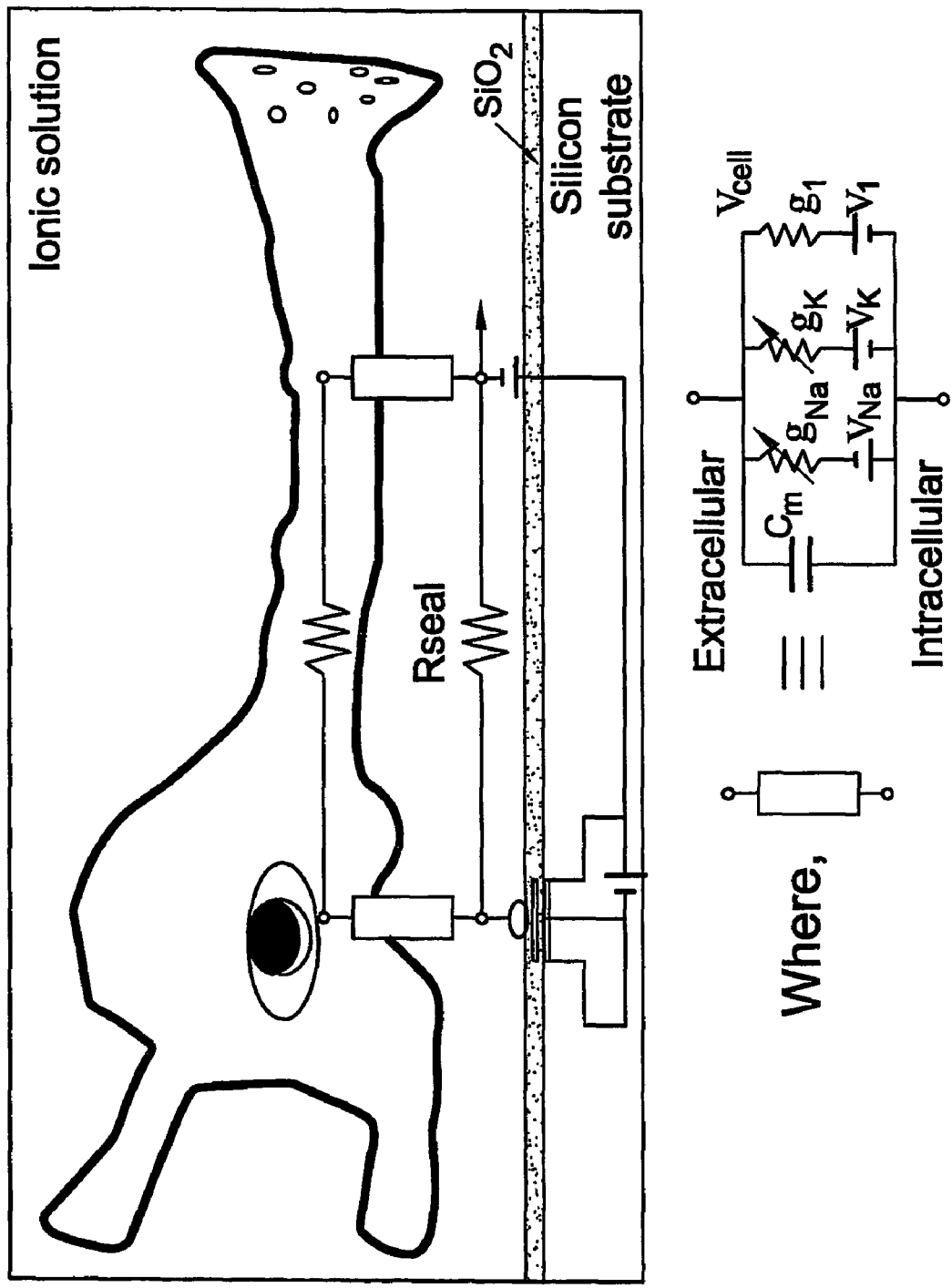
FIG. 2 illustrates a scheme defining the geometrical relations between a cultured neuron and the transistor gate, and a seal resistance between the body of the biological solution and the neuron-transistor coupling area.

Referring to FIG. 2, there is illustrated a scheme defining the geometrical relations between a cultured neuron and the transistor gate, and a high seal resistance $R_{seal}$ between the body of the biological solution and the neuron-transistor coupling area. The inventors investigated the parameters that determine the efficiency of the coupling coefficients and recognized the following major obstacles in constructing efficient, reliable and durable neuro-electronic hybrids:

the formation of the high seal resistance ($R_{seal}$) between the body of the biological solution and the neuron-transistor coupling area; and
  the continuous mobility and structural plasticity of the neurons relative to the coupling electrodes of the electronic devices.

1.1 Seal Resistance

The seal resistance depends on the dimensions of the space formed between the transistors floating gate surface and the plasma membrane facing the gate. The geometry and dimensions of this space defines the value of the seal resistance $R_{seal}$ formed between the center of the neuron-gate contact area and the non-contacting region. Theoretical considerations [2-4], as well as experimental considerations show that the larger $R_{seal}$, the better the electrical coupling. Hence, an electronic device should be designed so as to provide reliably increased $R_{seal}$.

1.2 Continuous Mobility and Structural Plasticity of Neurons

A characteristic feature of neurons is their structural plasticity. Under in vivo conditions neurons change their morphology and connectivity during development, after injury and in relation to various forms of learning and memory processes. Likewise, cultured neurons do not maintain a constant position on the device surface [5]. This mobility results in continuous translocation of the cell body, axons and dendrites in respect to the device surface. As a consequence, instability in the shape and amplitude of the recorded potential occur. Additionally, a large fraction of cultured neurons is often not forming an appropriate physical contact with the sensing device and thus functional contact with the surface electrodes is not established. In an experiment setting and for a small number of large neurons, this problem might be solved by creating a mechanical "Fence" in the form of a set of polymer pillars that surround the neuron and prevent it from moving away from its location. However in actual practice and in a multi-transistor array, individual neurons cannot be specifically placed within the "fence", and therefore the electronic device should be designed so as to reduce neuronal translocation.

The technique of the present invention takes an advantage of such known phenomena as phagocytosis, for designing an electronic device (transistor) for communication with living cells. Phagocytosis consists of a process of engulfing foreign particles by cells, and presents a phenomenon of fundamental importance for a large number of cells types and organisms. It is known to be a mean to internalize food (in protozoa), cellular debris (macrophages and neutrophils) or specific signaling molecules. Phagocytosis is defined as the cellular process that leads to the internalization of large particles in the range of up to 0.5 µm.

2. Phagocytosis

FIG. 3A schematically illustrates the cellular mechanisms that underlie phagocytosis. Phagocytosis is an action dependent process in which extension of the plasma membrane around a particle, or the "sinking" of a particle into the cell leads to its internalization. Accordingly, the process is inhibited by cytochalasin, a toxin that interferes with the polymerization dynamics of actin filaments. Phagocytosis is triggered by the activation of receptors [6] such as Fc-receptors (that mediate the internalization of particles decorated by immunoglobulins), complement-receptors, integrins that mediate the uptake of particles coated with fibronectin [7], mannose receptors that internalize lectins coated particles [8] and others.

As shown in FIG. 3A, the main steps leading to the internalization of a particle by phagocytosis are as follows:

Step 1: The primary step that triggers phagocytosis is the interaction between the extracellular domains of a receptor molecule and the molecules presented on the target surface. This interaction tethers the target to the membrane (FIG. 3A, 1).

Step 2: Additional receptors are recruited to the target leading to increased contact between the target and the plasma membrane and initiate the extension of the plasma membrane around the particle (FIG. 3A, 2).

Step 3: Signaling from the cytoplasmic domain of the engaged receptors recruit cytoskeletal elements including Arp2/3 that nucleates actin filaments around the particle (FIG. 3A, 3).

Step 4: Actin filaments together with myosin generate the mechanical force to drive the process of particle engulfment into the cell.

Step 5: The plasma membrane surrounding the particle is pinched off from the plasma membrane (FIG. 3A, 5).

The detached plasma membrane that contains the particle is now free to move in the cytosol and fuse with endosomes.

A mechanism utilized in the present invention consists of internalization of the micronail which is an integral part of a surface-substrate, and provides for better anchor neurons to the surface-substrate. While phagocytosis of "stand-alone", the particle is totally engulfed by the cell, a process that requires the cell to close the membrane over the particle and form a sealed vacuole (which contains the particle—FIG. 3A, 4 in the present invention the engulfment is of a part of a protrusion part that is of a larger surface of "stand alone" particles). As shown in FIG. 3B, in contrast to the cellular mechanisms that underlie phagocytosis, the internalization of the micronail which is an integral part of the surface-substrate requires the cell "swallowing" the head of the micronail or both the head and the base of the micronail, while not "finishing off" the process of vacuole formation (FIG. 3B, compare 1 and 2), i.e. while not detaching itself from the membrane with the section of the engulfed particles within. This difference raises a series of questions related to whether or not the fact that the "pinching off" act is not executed, will interfere with the molecular mechanisms of adhesion The inventors have found that harnessing the mechanisms of phago/ endocytosis provides for anchoring neurons and improving the electrical coupling between the neuron and electronic (the gate electrode which forms a part of a transistor). The recognition event between the extracellular domain of the cellular component of the plasma membrane, and the recognition molecule that decorate the particle (or the micronail) is the initial and essential event in the cascade that leads to phagocytosis (the tethering of the external particle and the cell). It is known that similar mechanisms and proteins provide also the essential component for the assembly of adhesion junctions. Thus, similar molecular building blocks participate in the attachment of cells to the substrate and to particles that are then phagocytosed. Among the common structural components, just a few are mentioned: talin that binds both cytoskeletal and signaling molecules, vinculin and paxillin. This approach is supported by a number of experiments which demonstrate that if a legend mediating phagocytosis is present over a sufficient large substrate area, the cultured cells will attach to the substrate and form adhesion junctions.

In spite of the configuration of an unfinished phagocytotic event (i.e. that the vinculin is not "pinched off"), the junction formed between the cells and the micronail is stable. This junction is a functional connection between the electron/transistor and the cell (e.g., neuron) enabling signal transfer in at least one direction, either from the transistor to the cell or from the cell to the transistor through capacitive coupling.

EXAMPLE 1

Internalization of Coated Beads

A suitable model for realizing the principles of internalization of the micronails heads is the internalization of beads. The inventors have developed optimal surface chemistry that induces neurons to phagocytose polystyren beads with diameters ranging between 0.2-0.5 μm. To this end, the following was carried out:

Using cultured Aplysia neurons, vertebrate cell lines (that can be induced to differentiate into neurons) and commercially available polystyrene beads with active surface; covalently lining hydrolytic enzymes to the beads thus facilitating degradation of the extracellular matrix and allowing the formation of intimate physical contact between the beads surface and receptor molecules located on the external surface of the plasma membrane; linking molecules that recognize plasma membrane receptors and tether it and facilitate phagocytosis, using adhesion molecules that stabilize the binding of the cell's plasma membrane to the pins base and its surroundings. The results in terms of successful phagocytosis and cell survival were evaluated by confocal microscope imaging supplemented by electron microscopy.

EXAMPLE 2

Induction of Endocytosis by Fragments of Neuronal Cells

Figure 4A:
FIGS. 4A-4D illustrate electron micrographs of endocytotic/phagocytotic profiles induced by the exposure of cultured Aplysia neurons to fragments of other cells, wherein FIG. 4A corresponds to the induction of endocytosis.
Figure 4B:
Figure 4C:
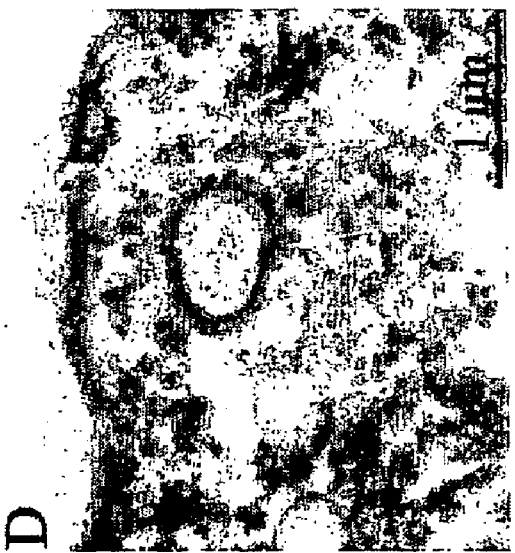
Figure 4D:

FIGS. 4A-4D illustrate the results (electron micrographs of endocytotic phagocytotic profiles) of another experiment performed by the inventors where the assembly of the sub-membrane coat and endocytosis was induced by exposing cultured Aplysia neurons to fragments of other neurons. FIG. 4A shows the induction of endocytosis, where "1" denotes an initial stage, noting the darkening of the membrane just beneath the particle on the right hand side of the micrograph, "2" corresponds to the state when plasma membrane begins to invaginate, and "3" notes the increase curvature of the plasma membrane. FIG. 4B shows the induction of an endocytotic profile by a particle. It appears as if the cell is sending an extension in support of the engulfment process. FIG. 4C shows the endocytotic profile. FIG. 4D shows a coated vesicle containing a cell fragment. The dimensions of the profile and coated vesicle are 0.3-0.5 μm, the dimensions of the golden head of the micronails.

EXAMPLE 3

Construction of a Transistor

Figure 6:
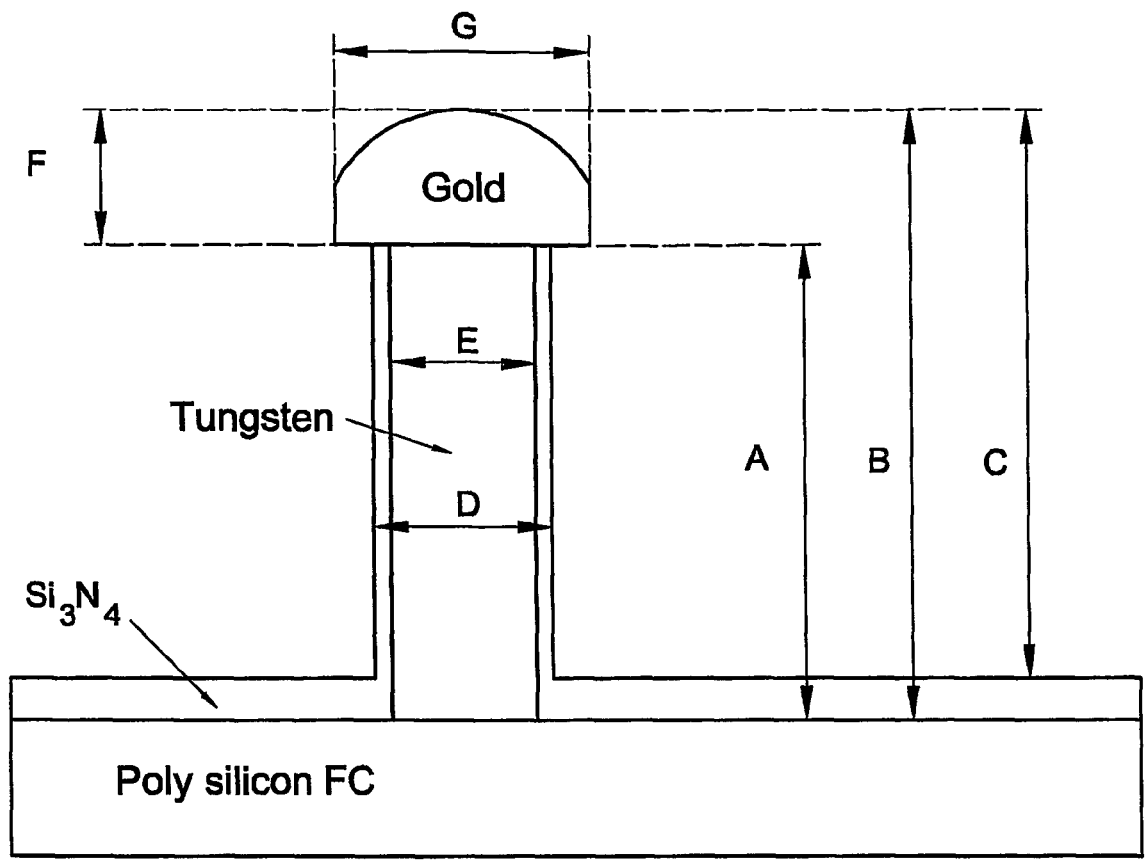

FIGS. 5 and 6 illustrate an electronic device (transistor) according to the invention utilizing a gate electrode (polysilicon floating gate in the present example) formed with micronails, which are protruding from gate electrode surface. FIG. 5 shows an over view of the micronails configuration on the floating gate, and FIG. 6 shows the scaled cross-section of the 'nail' structure. As shown, many micronails are provided protruding from a single gate.

The realization of the nails can be done either in 0.18 μm or 0.13 μm CMOS processes by minor modifications of the commonly used tungsten plugs technology. The following Table I presents values of the different dimensions of the micronail for these two technologies:

| CMOS Technology | Dimensions in μm | | | | | | | ASPECT Ratio |
|---|---|---|---|---|---|---|---|---|
| | A | B | C | D | E | F | G | |
| 0.18 μm | 0.805 | 0.960 | 0.920 | 0.290 | 0.250 | 0.155 | 0.40 | 3.17 |
| 0.13 μm | 0.610 | 0.740 | 0.700 | 0.240 | 0.20 | 0.130 | 0.335 | 2.91 |

For the purposes of this experiment, the base (stem-like portion) of micronail type A is preferably made of tungsten (but generally from any other suitable electrically conductive material) and is electrically isolated from the solution in which the neurons (or other cell types) are embedded by a layer of silicon nitride of about 20 nm in thickness. The top surface of the poly-silicon around the nails, in the plane of the transistor, is isolated from the solution by a layer of silicon nitride of about 40 nm. On top of the tungsten base, there is a cap (head portion) of gold or another metal such as for example copper, aluminum, platinum and silver, obtained by standard electroplating or electrolyses plating technique, which is performed on the finished wafers. An alternative process for the formation of the metal cap is by the use of standard lithography.

EXAMPLE 4

Construction of FGDT

Figure 7:
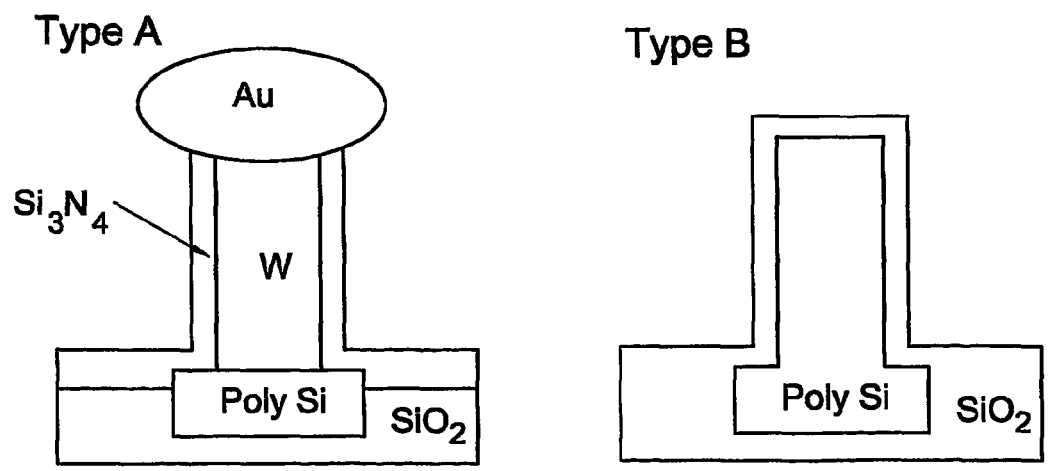
FIG. 7 illustrates two types of the Floating Gate Depletion-type Transistor (FGDT) based micronails sensors: Type A devices designed to enhance contact with neurons by applying various surface chemistries that facilitate wrapping of the nails by the cell's membrane, and Type B devices presenting a modification of the type A devices and being tailored to enhance sensitivity to molecular recognition events and chemical processes, with or without cells presence.

FIG. 7 shows two types of the Floating Gate Depletion type Transistor (FGDT) based micronails sensors: Type A devices are designed to enhance contact with neurons by applying various surface chemistries that facilitate wrapping of the nails by the cell's membrane, and Type B devices present a modification of the type A devices and are tailored to enhance sensitivity to molecular recognition events and chemical processes, with or without cells presence. Both FGDT types are fabricated using standard CMOS processing steps.

Additional layers of chemically active molecules can be added on top of the nail head to enhance the swallowing of the micronail's head into the neuron, as will be described further below.

A major concern of the micronails structure of the present invention is the influence of the nail on the neuron-transistor electrical coupling by short-circuiting the floating gate (FIG. 5). This is relevant only to floating gates connected to micronails that are not engulfed by a neuron.

Generally, two cases are to be considered: In one case, the exposed nail simply shorts the floating gate to the biological solution via the gold head. In the second case, there is an isolating layer (of about 20 nm thickness) over the entire nail surface including the gold head. This insulating layer still increases significantly the capacitive coupling of the floating gate to the ionic solution, consequently reduces the electrical coupling of the neuron to the floating gate by other nails that are engulfed by the neuron. The problem of coupling can be solved in one of the following ways:

1. By creating a single micronail on each floating gate;
2. By creating a closely packed cluster of micronails on each floating gate, the dimension of this cluster being less than a few microns, which will reduce the chances that one or more of the nails, will not be surrounded by the cell membrane.

The development of bioelectronic enzyme applications requires the immobilization of active proteins onto solid or colloidal substrates such as gold. Proteins adsorb nonspecifically onto clean gold surfaces with denaturation and a reduction of their activity [10]. Direct adsorption neither discriminates among protein populations nor controls their orientation, features sometimes desirable for an immobilization protocol. Coverage of the gold surface with alkanethiol self-assembled monolayers (SAMs) [11] has made it possible to drastically reduce nonspecific adsorption of proteins [12], to direct the binding of proteins to gold supports, and to control their orientation by using SAMs with ligands complementary to specific binding sites on native proteins [13]. Many strategies for protein immobilization on SAMs have been based on previous developments of chromatography supports, which oriented immobilized proteins through charged, hydrophobic, or other affinity group interactions [14]. Another known application of SAMs is the use of specific cofactor-apoprotein interactions to assemble enzymes on gold surfaces [5]. Also proteins have been modified, by genetic [16 or chemical procedures, so as to acquire binding sites with affinity for ligands on the monolayer. Electrostatic and hydrophobic interactions have also been used in protein immobilization procedures on gold electrodes modified with SAMs of thiols.

The technique of the present invention provides two new approaches applicable to native proteins. The first approach is to introduce programmed lifetime of enzymes via the use of biodegradable linkers, and the second approach relies on durable aromatic linkers that enhance the electronic coupling of molecular recognition events to the gold (or oxide) containing floating gate (vide infra).

Micronails Type A

As mentioned above, the type A micronails are fabricated from biocompatible metals, for example tungsten rods that are integral part of the gate but insulated from the surrounding by oxide or nitride layers. The bases of the nails are terminated with gold hemispheres (FIG. 7). The molecular decoration of these nails is differentiated according to the various exposed surfaces: gold for the heads and nitride or oxide for the bases. The molecularly modified gold heads present to the cultured cells plasma membrane chemical signals that facilitate its physical uptake by phagocytotic or endocytotic mechanisms (as described above with reference to FIGS. 4 and 5). The component of the self-assembled monolayers containing nitride base acts as the cell adhesion interfaces.

Micronails Type B

The nails in this case (FIG. 7) are fabricated from polysilicon rods/bases or other combinations of conductive layers that are integral part of the transistor gate. However, they are insulated from the surrounding by a thin insulating layer that is formed on top of the rod following etching of the nitride layer. In contrast to type A devices, here the surface area of the floating gate thermal-oxide coating is maximized to allow better molecular sensing ability and polarization mediated potential sensing. A layer of moieties that promote internalization is present on the coating (not-shown in the figure).

EXAMPLE 5

Functionalization of Micronails by Molecules

The technique of the present invention aimed at promoting the internalization of the micronails heads is based on their functionalization by molecules that perform at least one of the following three functions:

(a) Hydrolytic enzymes that facilitate degradation of the extracellular matrix (ECM) and thus allow intimate physical contact between the micronail head surface and receptor molecules located on the external surface of the plasma membrane;
(b) Molecules that recognize plasma membrane receptors and tether them and facilitate phagocytosis or endocytosis of the micronails head, i.e., leading to partial internalization of the micronails by the plasma membrane;
(c) Adhesion molecules that stabilize the binding of the cell's plasma membrane to the nails base and its surroundings.

Hydrolytic Enzymes

Figure 8:
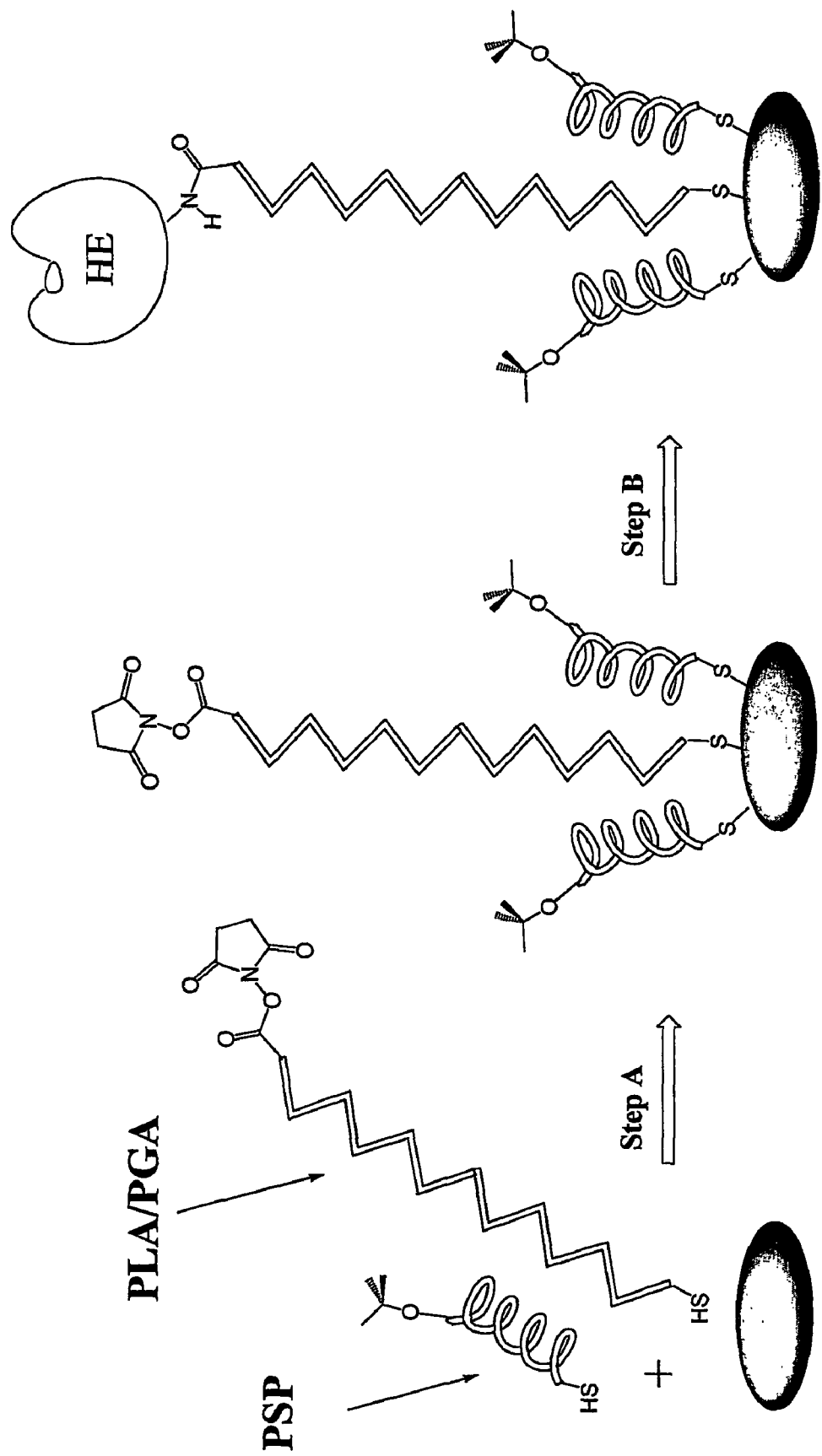
FIG. 8 illustrates a process of adhering hydrolytic enzymes to the nails surface, showing the micronails' head assembled with phagocytosis signaling peptides (PSP) and hydrolytic enzymes (HE) connected via biodegradable spacer (PLA/PGA)

FIG. 8 illustrates a process of adhering hydrolytic enzymes to the nails heads surface, showing the micronails' head assembled with phagocytosis signaling peptides (PSP) and hydrolytic enzymes (HE) connected via biodegradable spacer (poly(lactic-acid)—PGA or poly(gluconic-acid)—PGA). These hydrolytic enzymes include: polysaccharide-degrading enzymes (e.g., sialidase, neuraminidase, hyaluronidases and the like), proteinases including carboxypeptidase and collagenases, and lipid-degrading-enzymes (e.g., lipases and phospholipases).

The lifetime of the hydrolytic enzymes anchored to the gold hemisphere is limited by biodegradability (or "spontaneous" hydrolysis) of the linker chains. The implanted enzymes do not affect the phagocytosis signaling peptides. The biodegradable linker chain is synthesized from poly(lactic-acid) (PLA) or poly(gluconic-acid) (PGA) that are non-substrates for the HE used in here. The enzymatic hydrolysis is directed towards saccharides, lipids, and peptides of the ECM that would not attack the lactonic- (or gluconic-) ester bond. In order not to hydrolyze the phagocytosis signaling peptides, carboxypeptidase A is used as the peptide digesting enzyme and the phagocytosis signaling peptides is anchored to the surface through the N-terminal and blocked by t-Bu group at the C-terminal preventing the enzyme recognition and hydrolysis.

Tethering and Induction of Nail's Head Internalization

Following the local hydrolysis of the ECM, the recognition of plasma membrane surface molecules by molecules anchored to the gold head of the micronails is expected to internalization of the micronail nevertheless not including the final "pinching off" step featured by standard phagocytosis.

Figure 9:
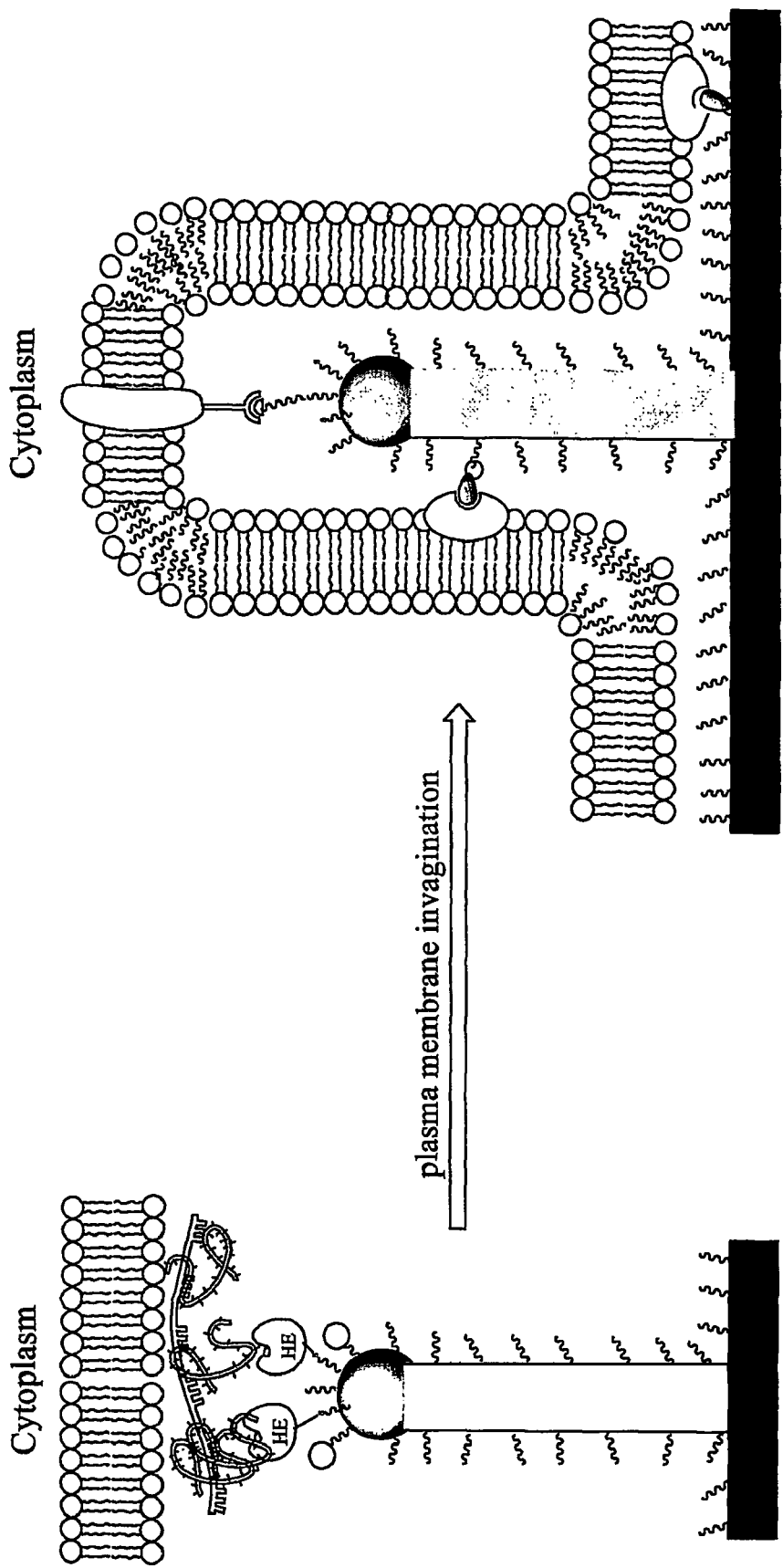
FIG. 9 shows the degradation of the extracellular matrix and partial phagocytosis of the nails by plasma membrane invagination.

This event is facilitated by anchoring to the gold head. This is illustrated in FIG. 9 showing degradation of the extracellular matrix and partial phagocytosis of the nails by plasma membrane invagination.

Hyperpolarizable molecular transducers can be assembled directly on the nail's Au (type A) or $SiO_2$ (type B) exposed area and their head groups anchor plasma membrane surface molecules. Integrins typically recognize short linear amino acid sequences in ECM proteins, one of the most common being Arginine-Glycine-Aspartate (RGD). Such peptides are grafted onto the gold surfaces via attachment at the N-terminal to surface grafted active ester.

Figure 10:
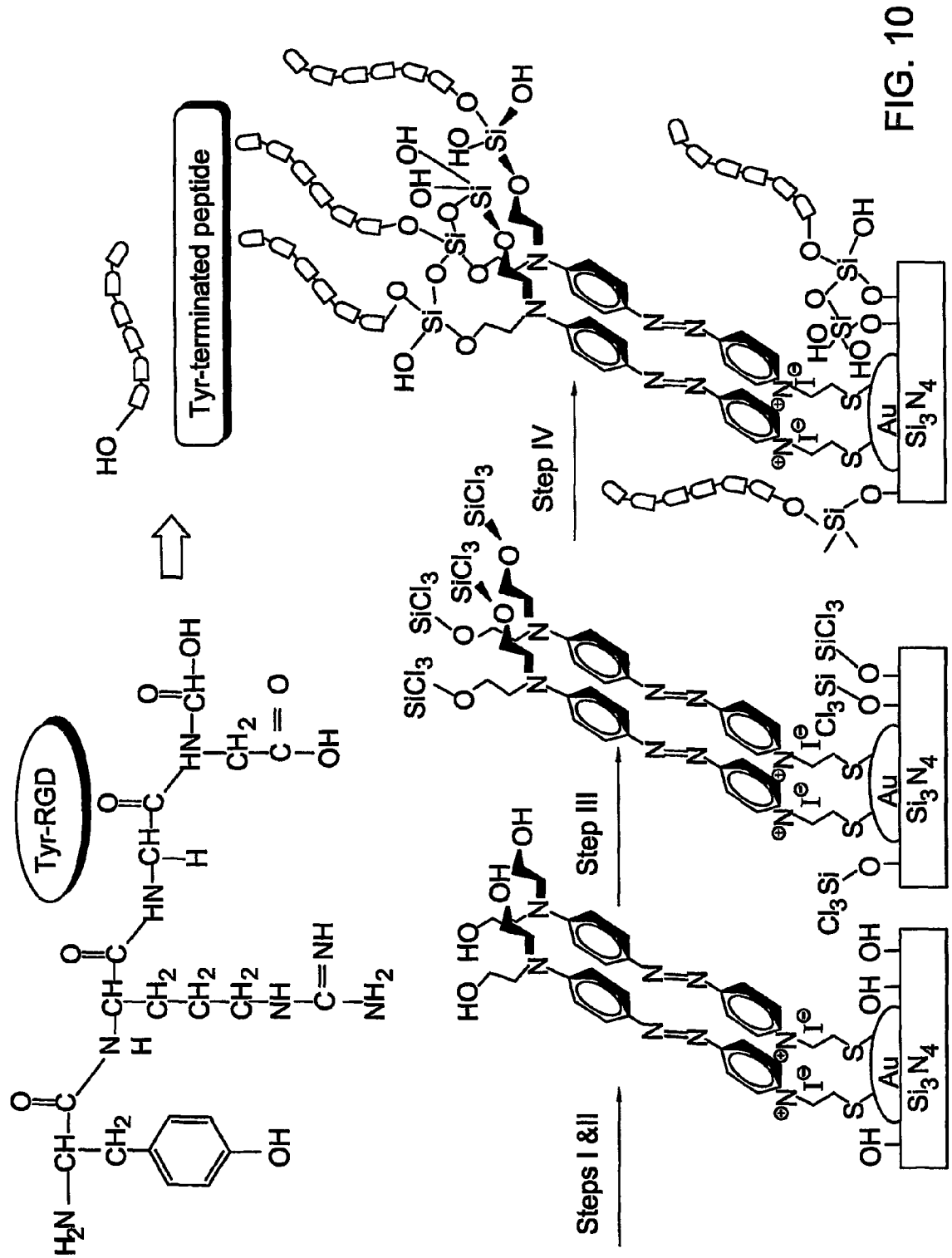
FIG. 10 exemplifies the technique of peptide anchoring to the nitride regions and to the gold nail-heads containing chromophoric layer, in type A devices, while type B devices will couple alkylhalide functionality to the oxide in step i, followed by steps ii-iv of this figure.

FIG. 10 illustrates peptide anchoring to the base, nitride regions and to the gold nail-heads containing chromophoric layer, in type A devices. In case of type A devices, chromophores containing surfaces are also grafted with peptides. In the case of type B devices, chromophores containing surfaces are assembled on $SiO_2$ surfaces by treating the surface with the appropriate coupling agent (e.g., 3-bromopropyl (trichlorosilane)), and thus the device will couple alkylhalide functionality to the oxide in step i, followed by steps ii-iv as shown in the example of RGD coupling of FIG. 10.

Figure 11:
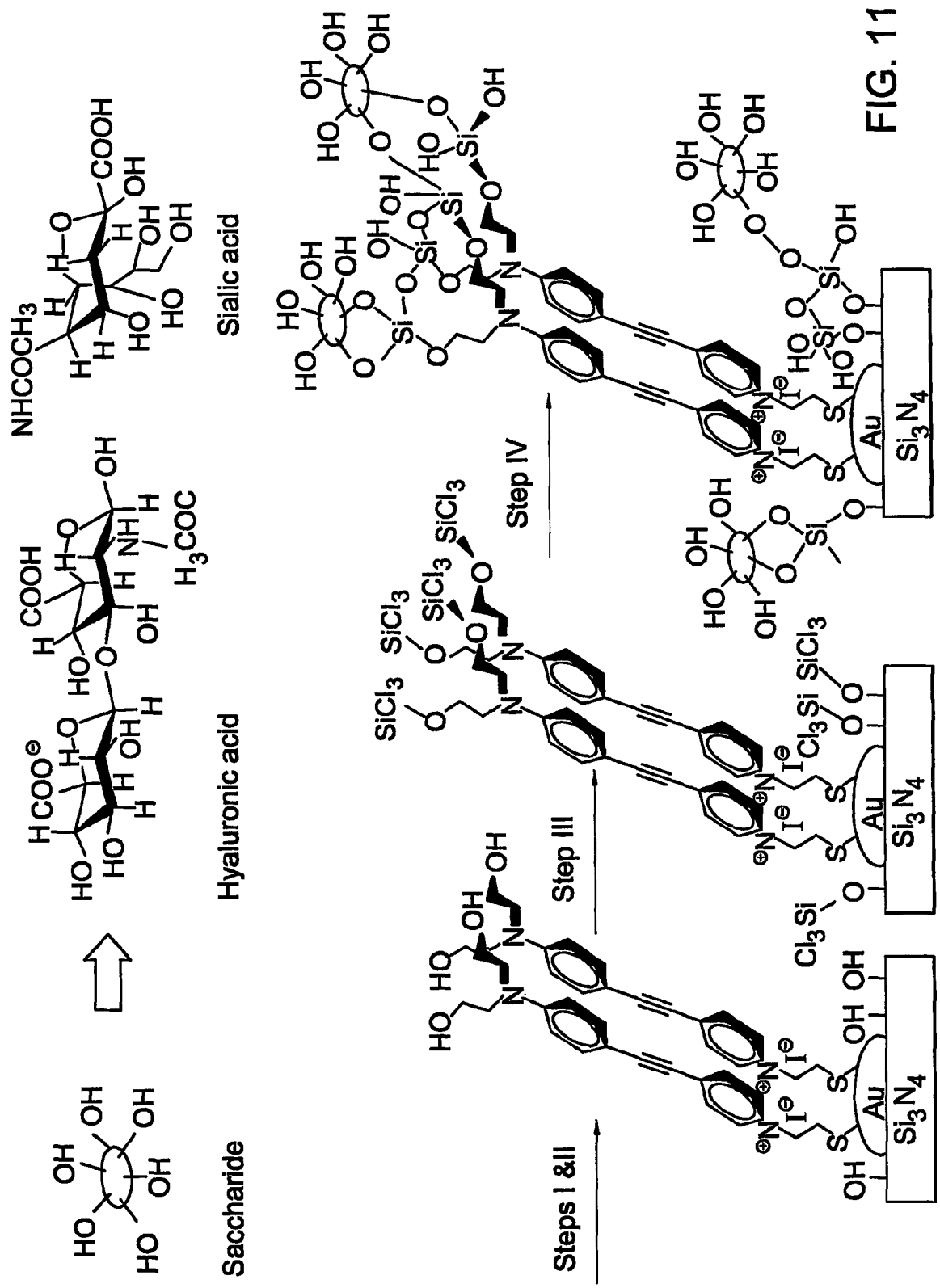
FIG. 11 exemplifies saccharides anchoring to the nitride regions and to the gold nail-heads containing chromophoric layer, in type A devices, while type B devices will couple alkylhalide functionality to the oxide in step i, followed by steps ii-iv of this figure.

The second approach according to the invention for creating intimate neuron-nail contacts relies on recognition sites of hyaluronan, the polysaccharide part of proteoglycan in the extracellular matrix. The glucosaminoglycan repeating unit of hyaluronan or sialic acid can be easily coupled via siloxane linkages of the sugar's hydroxyl-group. This coupling can be conducted directly on the nitride surface and via chromophoric layer self-assembled on the gold-heads in type A devices and on the oxide rods in type B devices. This is illustrated in FIG. 11, showing saccharides anchoring to the nitride regions and to the gold nail-heads containing chromophoric layer, in type A devices. Type B devices will couple alkylhalide functionality to the oxide in step i, followed by steps ii-iv. Hyaluronic acid and Sialic acid coupling is given as a non-limiting example.

EXAMPLE 6

Production of Positively Charged Monolayers

Figure 12:
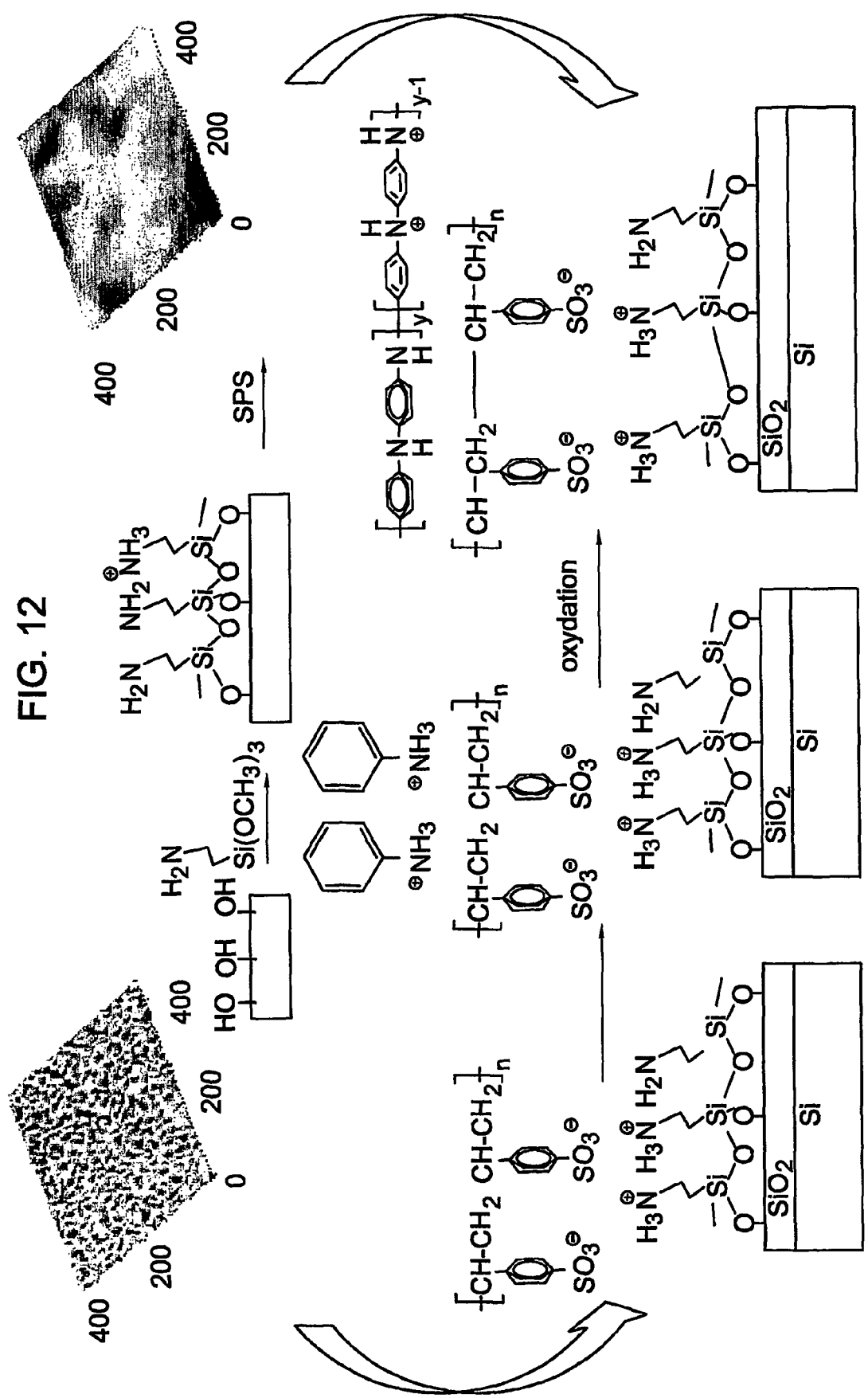
FIG. 12 illustrates the synthetic route developed for the chemical/enzymatic self-assembly of 2D-PAN monolayer, including AFM images of the PSS template layer (left) and the 2D-PAN (right) obtained via chemical oxidation.

The inventors have developed the 2D-PAN, a positively charged monolayer of polyaniline, to adhere the plasma membrane to the micronail stem and the active planes of the transistor (e.g., FGDT). The main steps of this method are illustrated in FIG. 12. The method relies on the electrostatic assembly of a monolayer of monomers (anilinium-ions) followed by their polymerization (to polyaniline, PAN). Polyanion (polystyrenesulfonate sodium salt, PSS) deposition has led to rougher surfaces than the small-molecules containing template layer. The electrostatic adhesion of the positively charged anilinium monomers is followed by chemical oxidation with ammonium-peroxydisulfate or enzymatically with horseradish-peroxidase (RRP) to yield the 2D-PAN. The use of PSS template layer for 2D-PAN self-assembly has created a special interface for neurons growth. The combination of positively charged (quaternary amines) and rough interface has led to very strong cell adhesion to the micronail.

The advantages of this layer over the standard neurophilic layers (e.g., laminine, poly-D-lysine, and fibronectin.) are associated with their diminished vertical dimensionality and reduced electrical resistivity. A better capacitive coupling between neurons and MOS-devices is provided when the neurons are placed closer to the sensing area (2-4 nm vs. few hundreds) and where the membrane potential is less shielded (conducting polymer vs. insulating layers). Thus, the coupling of the neurons to the nitride- and oxide-containing surfaces of the device should add to the sensitivity of both device types.

The assembly of 2D-PAN to gold surfaces has been developed [18] and can be straight-forward implemented to the micronail Au-head. The inventors have studied the warping of Au-nanoparticles (NP) with PAN-monolayers, and investigated their interface with Aplysia neurons. The adherence of Aplysia neuron to self-assembled PAN monolayer on an electrostatically bound Au-NP to positively charged glass substrate is illustrated in FIG. 13—an electron microscopy image of the interface between Aplysia's plasma membrane and a monolayer of 5 nm Au particles self-assembled with 2D-PAN monolayer on a glass substrate. The tight junction (of about 10-30 nm) is indicative of the decrease in $R_{seal}$ and the enhanced sensitivity of the micronail containing FGDT based neurosensors.

EXAMPLE 7

Chemical Synapses

Figure 14:
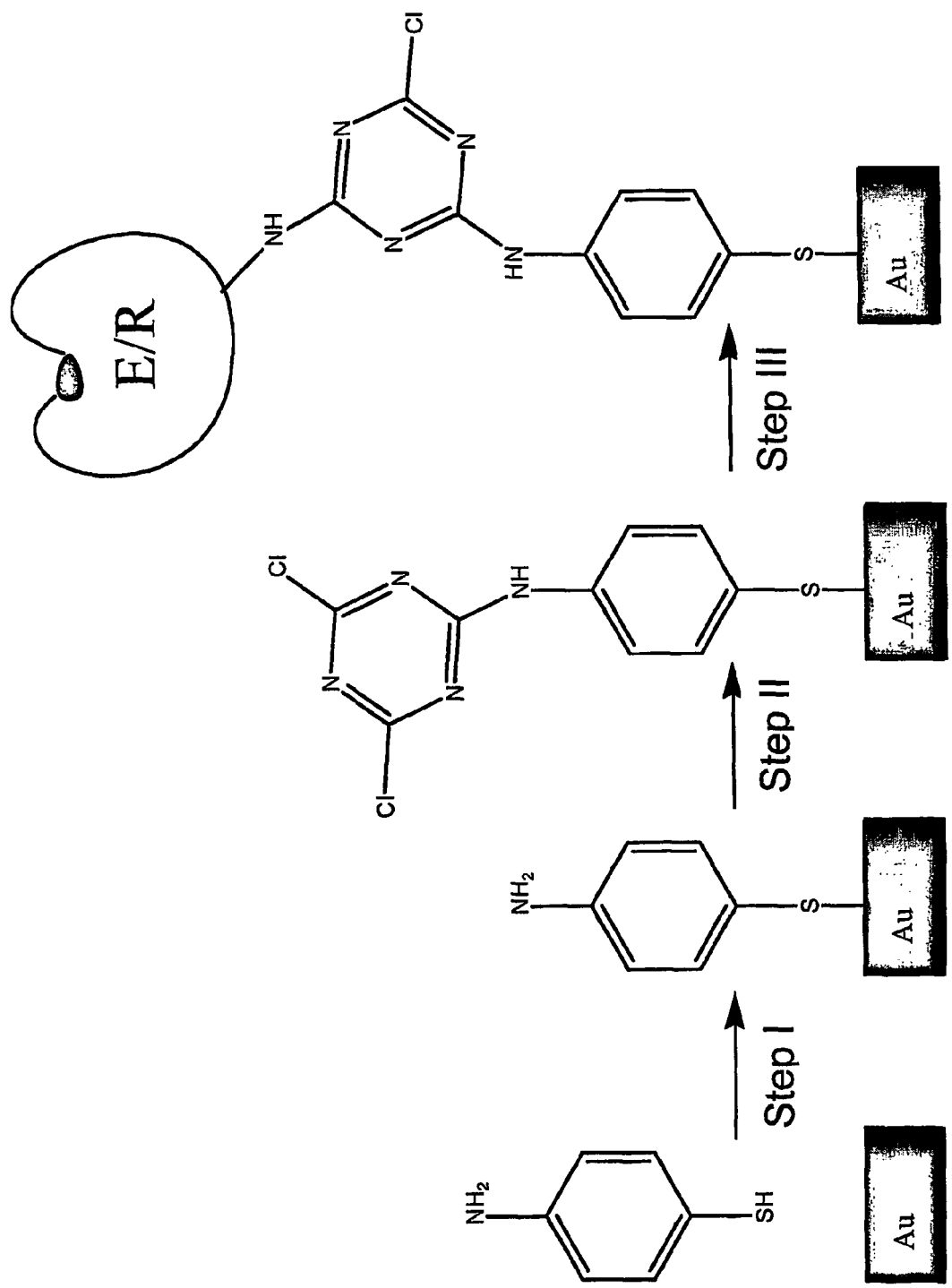
FIG. 14 exemplifies neurotransmitter site containing proteins (enzyme/receptor, E/R) anchoring to gold surfaces via rigid and short spacer (type A).

The chemical anchoring of receptors and enzymes can be conducted by covalent linkages to the gold nail binding by short and rigid coupling agent. FIG. 14 illustrates an example of a short and rigid molecular coupling of receptor or enzyme to the gold head by first assembling p-aminothiophenol followed by condensing cyanuric acid allowing coupling of the receptor/enzyme through amine condensation. In the present example, neurotransmitter site is shown containing proteins (enzyme/receptor, E/R) anchoring to gold surfaces via rigid and short spacer (type A). The assembly to oxide surfaces is conducted similarly excluding step i (type B), as disclosed in PCT/IL03/100941 assigned to the assignee of the present application, and incorporated herein reference.

As indicated above, the formation of chemical synapse composed of a neuronal presynaptic element and an electronic device that serves, as a post-synaptic element, enables to link neurons to the electronic device not only by electrical signals but also by released neurotransmitters and the electric device in such a case can detect said release. Such chemical linkage opens up a novel way to link the nervous system with the electronic world and allows simulating the natural way by which neurons as well as neurons and muscles communicate with each other. It should be emphasized in this respect the unidirectional communication between excitable cells is mainly executed by chemical synapses.

The inventors have developed a highly sensitive ($10^{-8}$ M) sensor for acetylcholine and conducted experiments in which polystyrene beads coated with bioactive molecules were shown to induce the ultrastructural differentiation of presynaptic terminal. The micronails surface can be coated with a variety of signaling molecules (as described above) and receptor molecules that recognize and binds acetylcholine, glutamate, GABA, serotonin and others.

The invention claimed is:

1. A substrate having a surface for adherence of cells thereto comprising:
    at least one micronail structure protruding from the surface, said micronail structure comprising a base rod-like portion and a head cap-like portion of a larger surface, wherein at least a region of said micronail structure on the head cap-like portion has cellular internalization-promoting moieties so that at least the head cap-like portion of the micronail structure has cellular-internalization promoting properties.

2. The substrate according to claim 1, wherein the head cap-like portion has the cellular internalization promoting properties.

3. The substrate according to claim 2, wherein the head cap-like portion is coated with the cellular internalization-promoting moieties.

4. The substrate of claim 2, wherein the head cap-like portion is composed of or coated with a metal containing material.

5. The substrate of claim 4, wherein the metal is selected from: gold, copper, aluminum, platinum, silver, or alloys of such metals or combinations of such metals.

6. The substrate of claim 1, wherein the cellular internalization-promoting moieties are hydrolytic enzymes that facilitate degradation of extracellular matrix, wherein the hydrolytic enzymes are selected from polysaccharide-degrading enzymes, proteinases and lipid-degrading-enzymes.

7. The substrate of claim 6, wherein said hydrolytic enzyme is connected to the micronail through a biodegradable spacer molecule.

8. The substrate of claim 1, wherein the cellular internalization-promoting moieties are molecules that recognize plasma membrane components, wherein said molecules are selected from: ligands of plasma membrane receptors or receptor binding-parts of said ligands; receptors that recognize plasma membrane components; lectins that bind to plasma-membrane glycoproteins; antibodies that recognize plasma-membrane components or binding fragments thereof; integrins that recognize short linear amino acid sequences in ECM proteins; and a combination of two or more of the above.

9. The substrate of claim 1, wherein the cellular internalization-promoting moieties are molecules that recognize plasma components and bind to polysaccharides that are part of proteoglycans in the ECM plasma membrane.

10. The substrate of claim 1, further comprising molecules that promote adhesion of cells.

11. The substrate of claim 10, wherein the molecules that promote adhesion of cells are present on at least one of the following: the base rod-like portion of the micronail, and the region surrounding the base rod-like portion.

12. The substrate of claim 10, wherein said adhesion molecules are in the form of a charged monolayer.

13. The substrate of claim 12, wherein said charged monolayer is a positively charged monolayer of polylysine, or polyaniline and a like.

14. . The substrate of claim 13, wherein said positively charged monolayer of polylysine or polyaniline is assembled on a polystyrenesulfonate layer, said polystyrenesulfonate layer comprising anion units connected through a linker to the micronail.

15. The substrate according to claim 1, adapted to form a cell-communicating part of an electrode.

16. The substrate according to claim 15, wherein the electrode is a gate electrode.

17. The substrate according to claim 16, wherein the micronail is a conductive rod, which is an integral part of the polysilicon gate electrode, and is insulated from the surrounding by a thin insulating layer.

18. The substrate according to claim 16, in the form of an integrated structure manufactured by lithography and etching techniques.

19. An electrode comprising the substrate of claim 15.

20. The electrode according to claim 19 being a gate electrode.

21. The electrode according to claim 20 having a single micronail.

22. The electrode according to claim 20 having a cluster of micronails.

23. The electrode according to claim 22, wherein the size of the cluster is smaller than the size of the cell to be in communication with the electrode.

24. A device for electrical communication with a cell comprising at least a pair of source-drain electrodes and at least one said gate electrode as defined in claim 20, thereby defining together at least one Field Effect Transistor (FET).

25. The electrode according to claim 19, wherein at least a region of said electrode is coated with a layer of immobilized recognition molecules that, in the presence of cell-secreted components, catalyze a reaction that causes release of ions in a media surrounding said recognition molecule.

26. The electrode according to claim 25, being a gate electrode.

27. The electrode according to claim 26, wherein the distance between the immobilized recognition molecules and the surface of the coated gate is smaller than 15 Å.

28. A device for the detection of cell secreting components comprising at least one pair of source-drain electrodes and at least one said gate-electrode of claim 27 forming together at least one Field Effect Transistor (FET).

29. The electrode according to claim 26, wherein said gate-electrode is an ion sensitive gate.

30. The electrode according to claim 29, wherein the ion-sensitive material is Aluminum Oxide ($Al_2O_3$), Silicon Nitride ($Si_3N_4$), Indium Tin Oxide ($In_3O_3Sn_2O_3$), Silicon Oxide ($SiO_2$) or Tantalum Oxide ($Ta_2O_5$).

31. The electrode according to claim 25, wherein the immobilized recognition molecules are enzymes or peptides.

32. The electrode according to claim 31, wherein the immobilized recognition molecules catalyze said reaction in the presence of a cell-secreted component selected from acetylcholine, glutamate, GABA, serotonin, neurotransmitters and/or neuroendocrines, growth factors, or cytokines.

33. The electrode according to claim 32, wherein said immobilized recognition molecule is acetylcholine esterase.

34. The electrode according to claim 25, wherein the immobilized recognition molecules are immobilized via linker molecules that are covalently bound to at least one of the surface of the substrate and the recognition molecules.

35. The electrode according to claim 34, wherein said linker molecules are selected from conjugated or unconjugated aliphatic, aromatic or heteroaromatic molecules, having at least one functional group capable of covalently binding to said surface and at least one functional group capable of covalently binding to said recognition molecules.

36. A device for the detection of cell secreting components comprising an electrode arrangement having at least one said electrode of claim 25.

37. A device for electric communication with a cell comprising an electrode arrangement having at least one said electrode of claim 19.

38. The device according to claim 37, wherein the electrical communication with the cell is achieved by a property selected from:
   (a) detecting the presence of currents, or current changes in cells;
   (b) detecting field potential or field potential change in cells;
   (c) providing a current to cells;
   (d) providing field potential to cells; or
   (e) a combination of two or more of (a) to (d).

39. The substrate according to claim 15, wherein the base rod-like portion of the micronail is electrically isolated from its surrounding.

40. The substrate according to claim 39, wherein the base rod-like portion of the micronail is made of tungsten, and is isolated from the surrounding by a layer of silicon nitrade.

41. The substrate according to claim 15, wherein the micronail is electrically isolated from its surrounding.

42. The substrate according to claim 1, wherein the micronail is configured and operable as a micro-syringe delivering material either to the plasma membrane or intracellularly.

43. The substrate according to claim 17, wherein the conductive rod is a poly-silicon rod.

* * * * *